US008485019B2

(12) United States Patent
Groves

(10) Patent No.: US 8,485,019 B2
(45) Date of Patent: Jul. 16, 2013

(54) METHODS AND SYSTEMS FOR ANALYSIS, REPORTING AND DISPLAY OF ENVIRONMENTAL DATA

(76) Inventor: Bruce D. Groves, Madison, NJ (US)

( * ) Notice: Subject to any disclaimer, the term of this patent is extended or adjusted under 35 U.S.C. 154(b) by 419 days.

(21) Appl. No.: 12/333,856

(22) Filed: Dec. 12, 2008

(65) Prior Publication Data

US 2009/0113990 A1    May 7, 2009

Related U.S. Application Data

(63) Continuation-in-part of application No. 11/644,755, filed on Dec. 22, 2006, now abandoned.

(51) Int. Cl.
*G01N 7/00* (2006.01)
(52) U.S. Cl.
USPC ........................... 73/23.2; 73/31.01
(58) Field of Classification Search
USPC ................................. 73/23.2, 31.01
See application file for complete search history.

(56) References Cited

U.S. PATENT DOCUMENTS

| | | | |
|---|---|---|---|
| 4,119,950 A | 10/1978 | Redding | |
| 4,526,028 A * | 7/1985 | Hu/bner | 73/23.2 |
| 4,704,607 A | 11/1987 | Teather | |
| 4,893,005 A | 1/1990 | Stiebel | |
| 4,920,263 A | 4/1990 | Fimian et al. | |
| 5,132,968 A | 7/1992 | Cephus | |
| 5,195,315 A | 3/1993 | Holladay | |
| 5,235,190 A | 8/1993 | Tucker et al. | |
| 5,406,265 A | 4/1995 | Trozzo et al. | |
| 5,428,964 A | 7/1995 | Lobdell | |
| 5,650,770 A | 7/1997 | Schlager et al. | |
| 5,761,908 A | 6/1998 | Oas et al. | |
| 5,786,767 A | 7/1998 | Serverino | |
| 5,786,768 A | 7/1998 | Chan et al. | |
| 6,072,396 A * | 6/2000 | Gaukel | 340/573.4 |

(Continued)

FOREIGN PATENT DOCUMENTS

| | | |
|---|---|---|
| EP | 0448360 A1 | 9/1991 |
| EP | 0527307 A2 | 2/1993 |
| FR | 2754911 | 4/1998 |
| JP | 2002351927 A * | 12/2002 |

OTHER PUBLICATIONS

USPTO, "Non-Final Office Action mailed Dec. 30, 2008", U.S. Appl. No. 11/644,755.
Machine Translation of FR 2754911, (Nov. 13, 2009), 6 pgs.

(Continued)

*Primary Examiner* — Hezron E Williams
*Assistant Examiner* — Rodney T Frank

(57) ABSTRACT

An environmental monitoring system and methods of a site are disclosed. The system includes one or more environmental measurement instruments, of which at least one instrument is capable to measure a concentration of particles in a certain size range. The system may also include an instrument that is capable of measuring a first concentration of particles in a first size range and a second concentration of particles in a second size range. The system may also include an instrument that is capable to measure a wind speed and a wind direction. The system may also include one device capable of recording an image of a location related to the site. The system includes a controller in communication with the one or more environmental measurement instruments, and a display device capable of displaying data generated by the one or more environmental measurement instruments. The system contains a network. Alerts can be provided based on conditions of the environment.

18 Claims, 17 Drawing Sheets

U.S. PATENT DOCUMENTS

| | | | |
|---|---|---|---|
| 6,114,964 | A | 9/2000 | Fasano |
| 6,252,510 | B1 | 6/2001 | Dungan |
| 6,598,464 | B1 * | 7/2003 | Rossi .................. 73/53.05 |
| 6,670,887 | B2 | 12/2003 | Dungan |
| 6,852,543 | B2 * | 2/2005 | Allen et al. .................. 436/122 |
| 6,868,314 | B1 * | 3/2005 | Frink .................. 701/3 |
| 6,889,009 | B2 | 5/2005 | Willebrand |
| 7,302,313 | B2 | 11/2007 | Sharp et al. |
| 7,463,142 | B2 * | 12/2008 | Lindsay .................. 340/539.12 |
| 7,495,774 | B2 * | 2/2009 | Hays et al. .................. 356/519 |
| 7,499,167 | B2 * | 3/2009 | Laudo .................. 356/417 |
| 2002/0144537 | A1 * | 10/2002 | Sharp et al. .................. 73/31.01 |
| 2005/0069482 | A1 * | 3/2005 | Allen et al. .................. 423/539 |
| 2006/0154642 | A1 * | 7/2006 | Scannell, Jr. .................. 455/404.1 |
| 2007/0097993 | A1 * | 5/2007 | Bojahra et al. .................. 370/401 |
| 2007/0109119 | A1 | 5/2007 | Zhang et al. |
| 2009/0090167 | A1 | 4/2009 | Groves |
| 2009/0113990 | A1 | 5/2009 | Groves |

OTHER PUBLICATIONS

USPTO "Final Office Action mailed Mar. 3, 2010", U.S. Appl. No. 11/644,755, 12 pgs.

Ex Parte Quayle Action mailed Jun. 11, 2010, U.S. Appl. No. 12/334,061, filed Dec. 12, 2008, 11 pgs.

"USPTO Final Office Action in related U.S. Appl. No. 11/644,755 mailed Nov. 2, 2009", 10 pgs.

"Dusttrak DRX Aerosol Monitor 8533", http://www.tsi.com/DUST-TRAK-DRX-Aerosol-Monitor-8533/ , 3 pages.

"Intro Dusttrak II and DRX Aerosol Monitors", http://www.tsi.com/News/News-Releases/2008/Introducing-DUSTTRAK-11-and-DRX-Aerosol-Monitors.aspx Jun. 1, 2008, 2 pages.

* cited by examiner

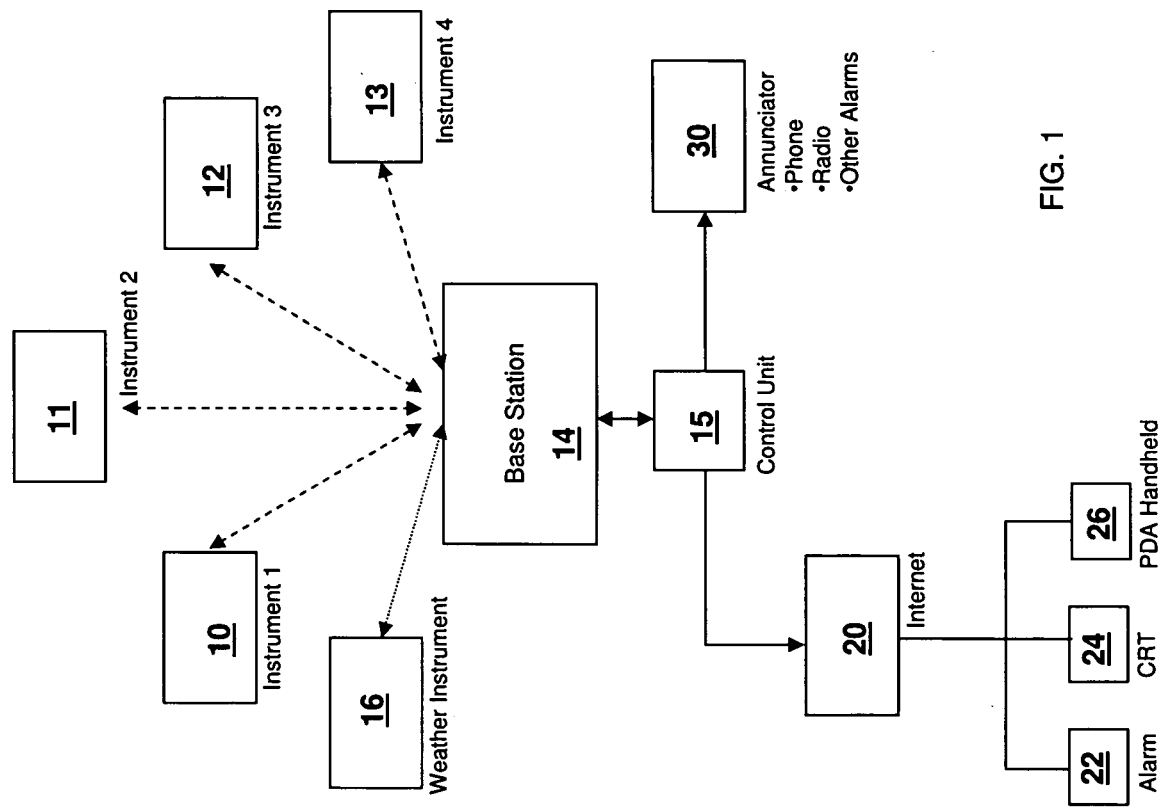

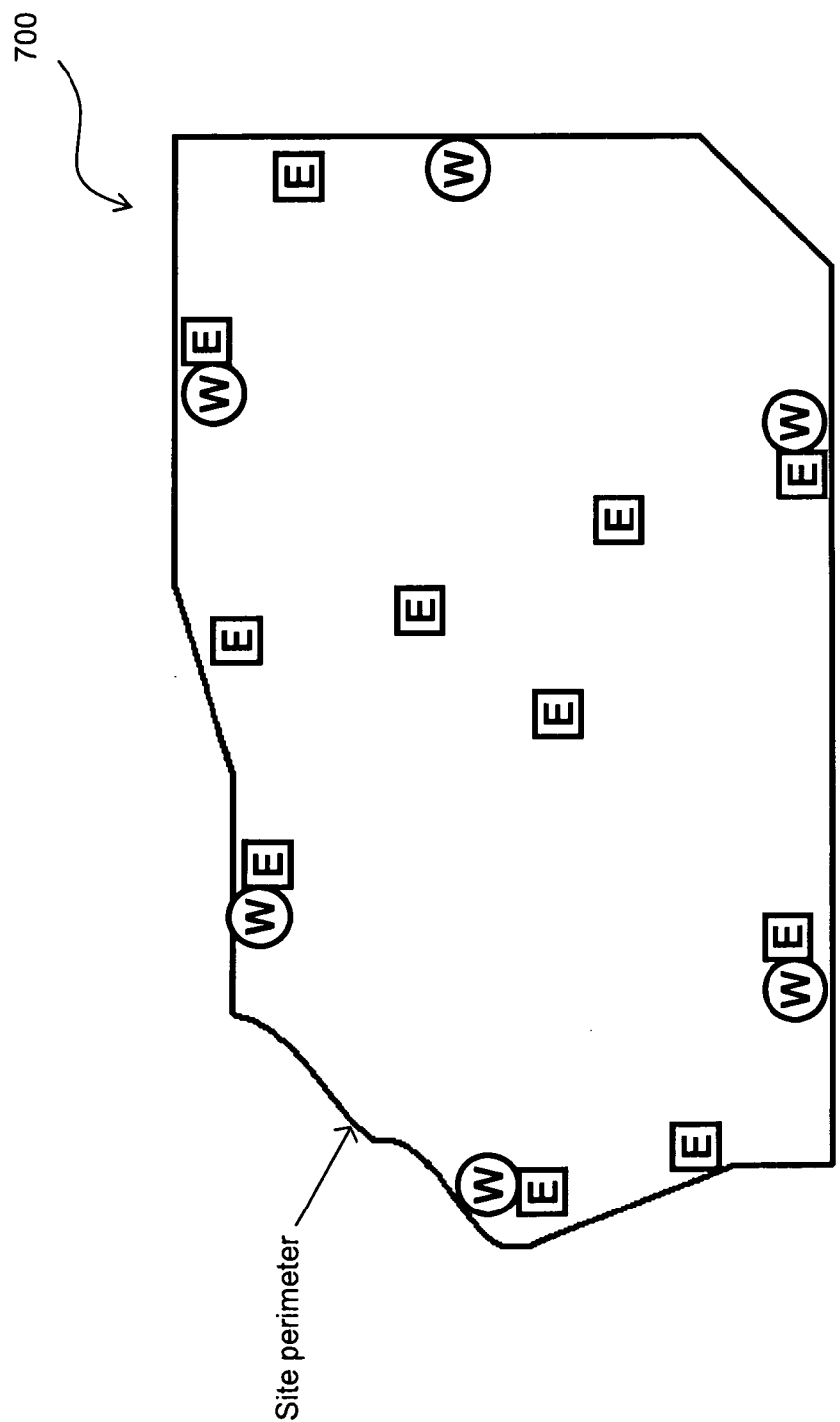

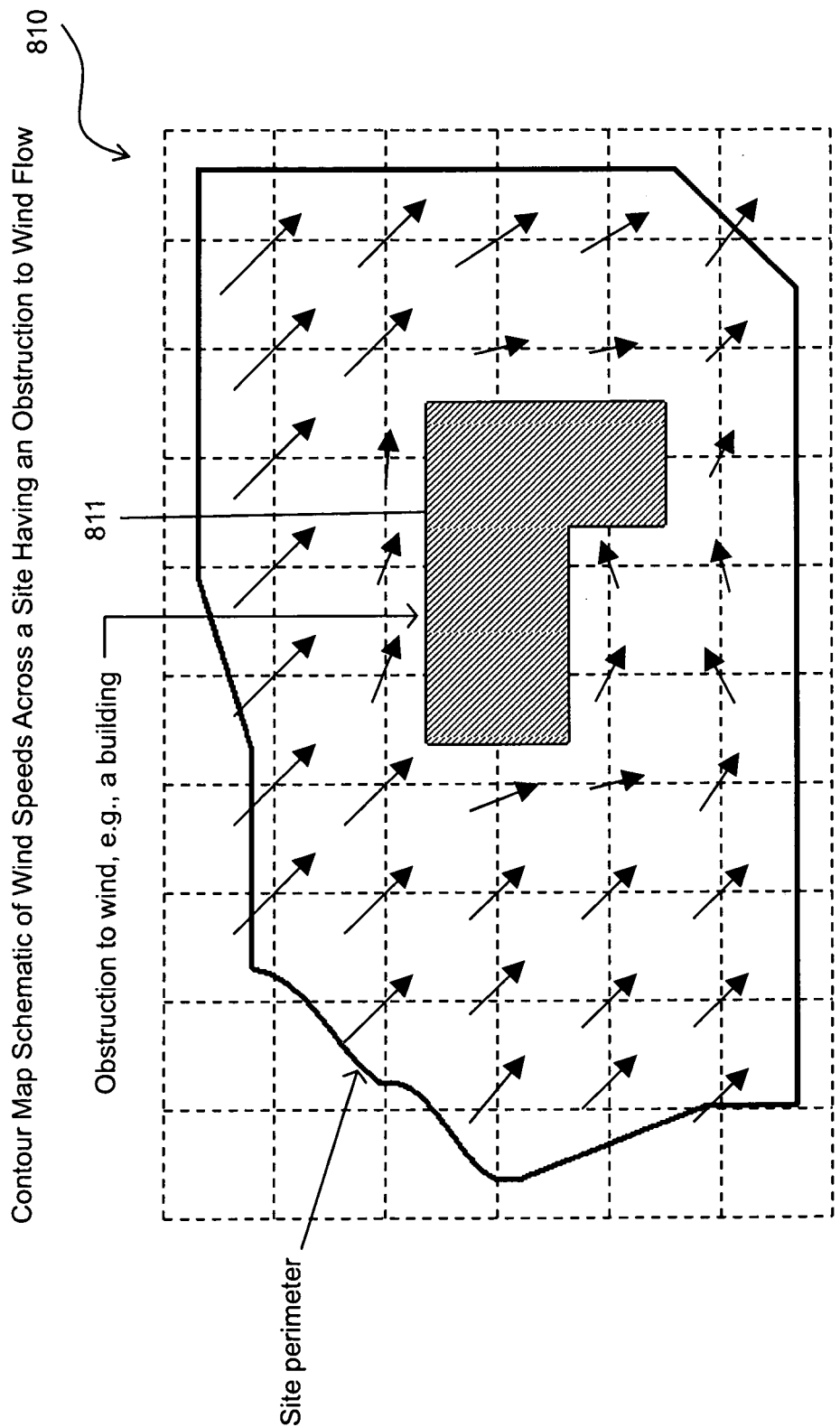

METHODS AND SYSTEMS FOR ANALYSIS, REPORTING AND DISPLAY OF ENVIRONMENTAL DATA

CROSS-REFERENCE TO RELATED APPLICATIONS

This application is a continuation-in-part of U.S. Non-Provisional patent application Ser. No. 11/644,755 filed Dec. 22, 2006, which is incorporated herein by reference in its entirety.

BACKGROUND OF THE INVENTION

The present invention relates to the monitoring of environmental conditions such as air quality and other physical annoyances and hazards, such as noise and radiation, for example, at construction sites, demolition sites, remediation sites and emergency sites.

Conventional approaches to real-time outdoor air monitoring suffer from lack of precision in identifying the sources of fugitive emissions. This is, in part, because real-time sensors often rely on detecting surrogate substances such as dust to infer the presence of the airborne agents of interest. In addition, existing commercially available products also lack the capability to effectively monitor the discrete changes of wind-induced air movements in real-time for a site under observation. For these reasons, conventional approaches to environmental monitoring cannot clearly distinguish contaminants of concern from other airborne substances that would be considered benign interferences and/or off-site, background emissions. Consequently, it may be difficult to set appropriate real-time environmental threshold limits based solely on the contaminants of concern because the sampling methodology is also sensitive to the various non-hazardous and/or background interferences.

The current approach to air monitoring may lead to false positives, inefficient implementation of environmental controls, inaccurate hazard assessments, and ineffective overall management of a site's environmental health program.

Accordingly, novel and improved systems and methods for analysis, reporting and display of environmental data are required.

SUMMARY OF THE INVENTION

The environmental/air toxic monitoring system of the present invention provides for the real-time monitoring, continuous data logging, and control of a plurality of communications-enabled monitoring instruments on a given site. In accordance with one embodiment of the present invention, up to 125 instruments can be provided per computer port. The system includes at least one measurement instrument that can measure a concentration of particles of a material in at least two ranges of sizes of particles. The system of the present invention can interface with a variety of instruments from a single control unit. In accordance with one embodiment this interface is provided via a serial communications capability. The system and method of the present invention can also calculate a variety of user-defined statistics while data logging, and providing real-time, usable data for immediate use. It further provides users with remote access to logged data and can communicate user-defined situations such as exceedences via telephone, email, computers, PDAs or other devices/media. It can also provide historical monitoring capabilities.

The environmental/air toxics monitoring system, in accordance with one aspect of the present invention, includes multiple components: An Instrumentation Pool with instruments 10, 11, 12, 13 and 16; a Communication System; a Base Station 14, which may include, for example, computer servers and other automated logic for acquiring, storing, and transmitting data; a Control Unit 15, which may include, for example, computer servers and other automated logic for storing, reporting and displaying data; Remote Access; and Annunciators 30, as shown in FIG. 1.

In accordance with an aspect of the present invention an environmental monitoring system is provided, comprising one or more environmental measurement instruments that collect a plurality of data including a measurement instrument being positioned in a location related to a site to be monitored and the measurement instrument being able to measure in real-time a concentration of particles in at least a first range of sizes and a second range of sizes and provide data on each of the range of sizes, a controller in communication with the one or more measurement instruments, and a device located remotely from the controller capable of displaying data generated by the one or more environmental measurement instruments.

In accordance with a further aspect of the present invention an environmental monitoring system is provided, further comprising the means to provide the location of various sampling points with geometric coordinates.

In accordance with yet a further aspect of the present invention an environmental monitoring system is provided, further comprising a database storing data collected from the one or more environmental measurement instruments, the data being provided with a time stamp and the geometric coordinates of the location of the one or more environmental measurement instrument.

In accordance with yet a further aspect of the present invention an environmental monitoring system is provided, further comprising one or more displays at the controller capable of displaying data generated by the one or more environmental measurement instruments.

In accordance with yet a further aspect of the present invention an environmental monitoring system is provided, wherein the device can display data generated by the one or more environmental measurement instruments graphically.

In accordance with yet a further aspect of the present invention an environmental monitoring system is provided, wherein the device can display a map of the site that identifies selectively a location of the one or more environmental measurement instruments and displays a concentration of particles in at least the first range of sizes and in the second range of sizes.

In accordance with yet a further aspect of the present invention an environmental monitoring system is provided, wherein the device can issue an alarm depending on the data generated by the measurement instrument.

In accordance with yet a further aspect of the present invention an environmental monitoring system is provided, further comprising storing in the database an environmental profile of a material including a concentration of at least two ranges of sizes of particles of the material.

In accordance with yet a further aspect of the present invention an environmental monitoring system is provided, wherein an alarm is provided when a concentration of at least two ranges of sizes of particles measured by a measurement instrument meets an alarm criterion.

In accordance with yet a further aspect of the present invention an environmental monitoring system is provided, comprising a measurement instrument being positioned in a location related to a site to be monitored and the measurement instrument being able to measure a concentration of particles in at least a first range of sizes and in a second range of sizes and to provide data on each of the range of sizes, a controller in communication with the measurement instrument and a display capable of displaying a map showing the location of the measurement instrument.

In accordance with yet a further aspect of the present invention an environmental monitoring system is provided, wherein the map also displays data collected by the measurement instrument.

In accordance with yet a further aspect of the present invention an environmental monitoring system is provided, further comprising a database storing data collected from the measurement instrument, the data being provided with a time stamp and the geometric coordinates of the location of the measurement instrument.

In accordance with yet a further aspect of the present invention an environmental monitoring system is provided, wherein the controller can issue an alarm depending on the data generated by the measurement instrument.

In accordance with yet a further aspect of the present invention an environmental monitoring system is provided, wherein the display and the controller have the capability of controlling the measurement instrument.

In accordance with yet a further aspect of the present invention an environmental monitoring system is provided, wherein the device can display a map of the site that identifies the location of the measurement instrument and can display a concentration of particles in at least the first range of sizes and in the second range of sizes of particle size measured at the location.

In accordance with yet a further aspect of the present invention an environmental monitoring system is provided, wherein the device can issue an alarm depending on the data generated by the measurement instrument.

In accordance with yet a further aspect of the present invention an environmental monitoring system is provided, further comprising storing in the database an environmental profile of a material including a concentration of at least two ranges of sizes of particles of the material.

In accordance with yet a further aspect of the present invention an environmental monitoring system is provided, wherein an alarm is provided when a concentration of one or more ranges of sizes of particles measured by the measurement instrument meets an environmental profile of a material.

In accordance with yet a further aspect of the present invention an environmental monitoring system is provided, further comprising one or more instruments at the location not measuring a concentration of particles in at least a first range of sizes and in a second range of sizes.

In accordance with yet a further aspect of the present invention an environmental monitoring system is provided, wherein the controller is in communication with the measurement instrument through a wireless connection.

In accordance with an aspect of the present invention an environmental monitoring system is provided, comprising one or more environmental measurement instruments that collect a plurality of data, including a measurement instrument being positioned in a location related to a site to be monitored and the measurement instrument being able to measure a variety of meteorological data, for example, a wind direction and a wind magnitude, a controller in communication with the one or more measurement instruments, and a device located remotely from the controller capable of displaying data generated by the one or more environmental measurement instruments.

In accordance with a further aspect of the present invention an environmental monitoring system is provided, further comprising at least one more measurement instrument being positioned in a second location related to a site to be monitored and the measurement instrument being able to measure a wind direction and a wind magnitude.

In accordance with yet a further aspect of the present invention an environmental monitoring system is provided, further comprising, a database storing data collected from the one or more environmental measurement instrument, the data being provided with a time stamp and geometric coordinates of the location of the one or more environmental measurement instruments.

In accordance with yet a further aspect of the present invention an environmental monitoring system is provided, wherein the system is capable of calculating a wind direction and a wind magnitude for a location from data of wind direction and wind magnitude of at least 2 other locations.

In accordance with yet a further aspect of the present invention an environmental monitoring system is provided, further comprising: one or more measurement instruments capable of measurement a concentration of particles of a material in at least one range of size of particles.

In accordance with yet a further aspect of the present invention an environmental monitoring system is provided, further comprising: one or more measurement instruments capable of measuring a concentration of particles of a material in at least a first and a second range of size of particles.

In accordance with yet a further aspect of the present invention an environmental monitoring system is provided, wherein the system is capable of associating a concentration of particles of a material at a location with a wind direction and a wind magnitude at the location.

In accordance with yet a further aspect of the present invention an environmental monitoring system is provided, further comprising one or more displays at the controller capable of displaying data generated by the one or more environmental measurement instruments.

In accordance with yet a further aspect of the present invention an environmental monitoring system is provided, wherein the device can display data generated by the one or more environmental measurement instruments graphically.

In accordance with yet a further aspect of the present invention an environmental monitoring system is provided, wherein the device can display a map of the site that identifies selectively a location of the one or more environmental measurement instruments, a wind direction and a wind magnitude related to the location and data provided by a measurement instrument related to the location.

In accordance with yet a further aspect of the present invention an environmental monitoring system is provided, wherein the device can display selectively environmental data related to two locations on a wind streamline.

In accordance with yet a further aspect of the present invention an environmental monitoring system is provided, wherein the system can issue an alarm depending on data generated by the measurement instrument.

In accordance with an aspect of the present invention a method for environmentally monitoring a site is provided, comprising collecting data from one or more environmental measurement instruments located at or near a site that is monitored including at least one instrument for measuring wind direction and wind magnitude at a location, communicating by a controller with the one or more environmental measurement instruments, and displaying data generated by the one or more environmental measurement instruments by a device located remotely from the controller.

In accordance with a further aspect of the present invention a method for environmentally monitoring a site is provided, further comprising storing data collected from the one or more environmental measurement instrument in a database, the data being provided with a time stamp and geometric coordinates of the location of the one or more environmental measurement instruments.

In accordance with yet a further aspect of the present invention a method for environmentally monitoring a site is provided, further comprising calculating a wind direction and a wind magnitude for a location from data of wind direction and wind magnitude in at least 2 other locations.

In accordance with yet a further aspect of the present invention a method for environmentally monitoring a site is provided, further comprising: measuring at a location a concentration of particles of a material in a range of size of particles.

In accordance with yet a further aspect of the present invention a method for environmentally monitoring a site is provided, further comprising: associating a concentration of particles of the material with a wind direction and a wind magnitude at the location.

In accordance with yet a further aspect of the present invention a method for environmentally monitoring a site is provided, further comprising identifying selectively on a display in a map a location of the one or more environmental measurement instruments, displaying a wind direction and a wind magnitude related to the location; and displaying data provided by an environmental measurement instrument related to the location.

In accordance with yet a further aspect of the present invention a method for environmentally monitoring a site is provided, further comprising displaying environmental data related to at least two locations on a wind streamline.

In accordance with yet a further aspect of the present invention a method for environmentally monitoring a site is provided, further comprising issuing an alarm depending on a concentration of a material and a wind direction.

In accordance with an aspect of the present invention an environmental monitoring system for monitoring a site is provided, comprising one or more environmental measurement instruments that collect a plurality of data, one or more image recording devices, each being capable of recording an image of a location related to the site, a controller in communication with the one or more environmental measurement instruments and with the one or more image recording devices, and a device located remotely from the controller capable of displaying data generated by the one or more environmental measurement instruments.

In accordance with a further aspect of the present invention an environmental monitoring system for monitoring a site is provided, wherein at least one environmental measurement instrument is capable of measuring a concentration, quantity or mass of a material, or a magnitude of noise or radiation.

In accordance with yet a further aspect of the present invention an environmental monitoring system for monitoring a site is provided, wherein at least one environmental measurement instrument is capable of measuring a wind direction and a wind magnitude.

In accordance with yet a further aspect of the present invention an environmental monitoring system for monitoring a site is provided, wherein at least one environmental measurement instrument is capable of measuring radiation.

In accordance with yet a further aspect of the present invention an environmental monitoring system for monitoring a site is provided, wherein the system is capable of initiating selectively the recording of an image by the one or more image recording devices.

In accordance with yet a further aspect of the present invention an environmental monitoring system for monitoring a site is provided, wherein the system initiates the recording based on data provided by at least one of the one or more environmental measurement instruments.

In accordance with yet a further aspect of the present invention an environmental monitoring system for monitoring a site is provided, wherein the system is capable of stopping selectively the recording of an image by the one or more image recording devices.

In accordance with yet a further aspect of the present invention an environmental monitoring system for monitoring a site is provided, further comprising a database storing data collected from the one or more environmental measurement instruments, the data being provided with a time stamp and geometric coordinates of a location of an environmental measurement instrument, the data being associated with the recording of an image.

In accordance with yet a further aspect of the present invention an environmental monitoring system for monitoring a site is provided, wherein an image can be selected for display by applying display criteria to the data associated with the recording of the image.

In accordance with yet a further aspect of the present invention an environmental monitoring system for monitoring a site is provided, wherein data related to a timestamp of an image are also displayed.

In accordance with yet a further aspect of the present invention a method monitoring a site by an environmental monitoring system is provided, comprising collecting a plurality of data by one or more environmental measurement instruments at a location related to the site recording of an image of a location related to the site by one or more image recording devices, communicating by a controller with the one or more environmental measurement instruments and with the one or more image recording devices, and displaying data generated by the one or more environmental measurement instruments by a device located remotely from the controller.

In accordance with yet a further aspect of the present invention a method monitoring a site by an environmental monitoring system is provided, wherein at least one measurement instrument is capable of measuring a concentration of a material.

In accordance with yet a further aspect of the present invention a method monitoring a site by an environmental monitoring system is provided, wherein at least one measurement instrument is capable of measuring a variety of meteorological data, for example, a wind direction and a wind magnitude.

In accordance with yet a further aspect of the present invention a method monitoring a site by an environmental monitoring system is provided, wherein at least one measurement instrument is capable of measuring radiation.

In accordance with yet a further aspect of the present invention a method monitoring a site by an environmental monitoring system is provided, wherein the recording of an image by the one or more image recording devices is initiated selectively.

In accordance with yet a further aspect of the present invention a method monitoring a site by an environmental monitoring system is provided, wherein initiating the recording is based on data provided by at least one of the one or more environmental measurement instruments.

In accordance with yet a further aspect of the present invention a method monitoring a site by an environmental monitoring system is provided, wherein the system is capable of stopping selectively the recording of an image by the one or more image recording devices.

In accordance with yet a further aspect of the present invention a method monitoring a site by an environmental monitoring system is provided, further comprising storing data collected from the one or more environmental measurement instrument in a database, the data being provided with a time stamp and geometric coordinates of a location of an environmental measurement instrument, the data being associated with the recording of an image.

In accordance with yet a further aspect of the present invention a method monitoring a site by an environmental monitoring system is provided, further comprising selecting an image for display by applying display criteria to the data associated with the recording of the image.

In accordance with yet a further aspect of the present invention a method monitoring a site by an environmental monitoring system is provided, further comprising displaying data related to a timestamp of an image.

DESCRIPTION OF THE DRAWINGS

FIG. 1 illustrates an embodiment of an environmental monitoring system in accordance with one aspect of the present invention;

FIG. 7 illustrates in diagram a map identifying a location of an instrument in accordance with an aspect of the present invention;

FIGS. 8a and 8b illustrate in diagram a map identifying wind direction and magnitude in accordance with an aspect of the present invention;

DESCRIPTION OF A PREFERRED EMBODIMENT

Figure 2A:
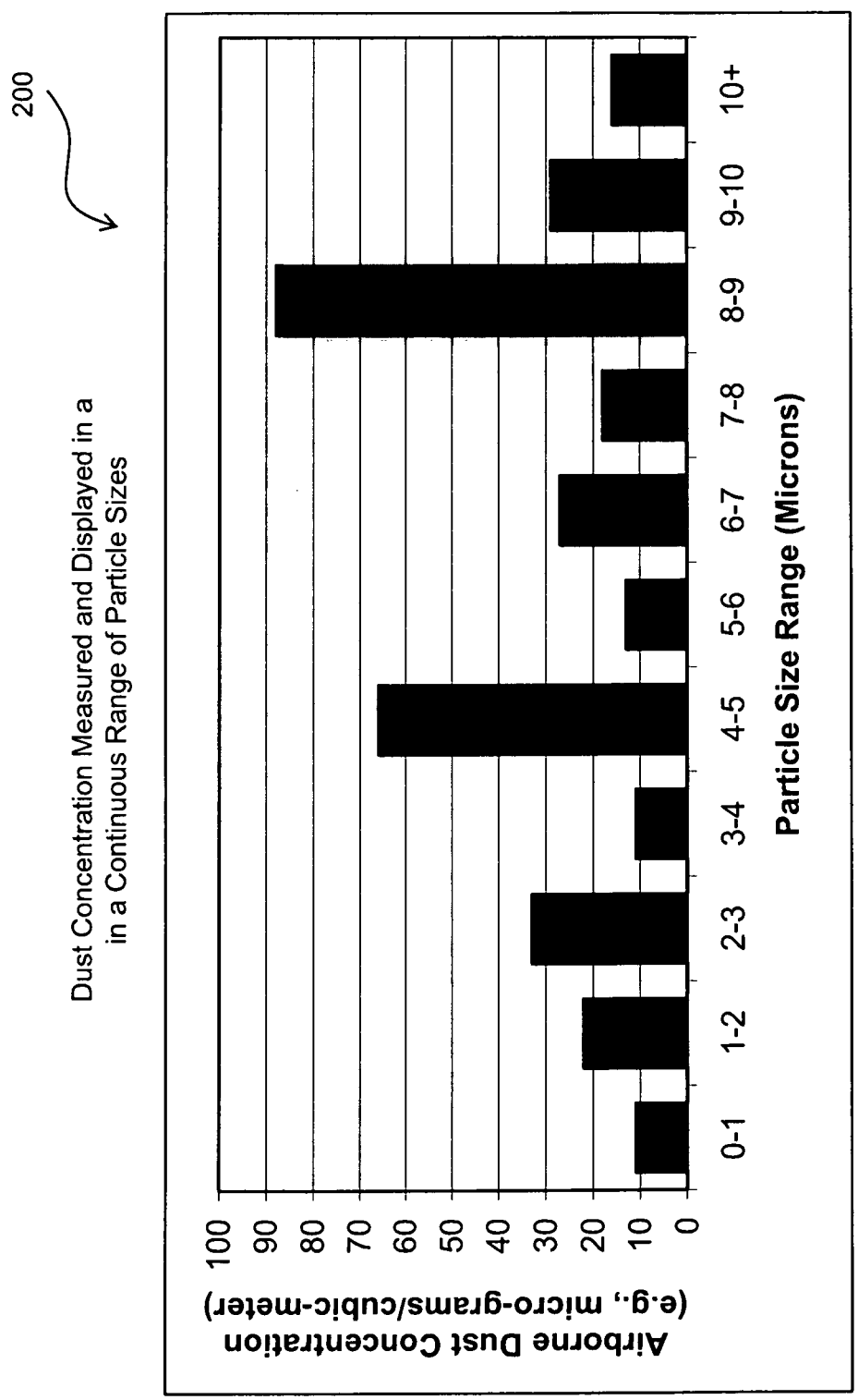
FIGS. 2a, 2b, 2c and 2d illustrate in a graph a distribution of particle sizes over different sizes in accordance with an aspect of the present invention.

Novel basic air monitoring systems and methods were invented and disclosed in U.S. patent application Ser. No. 11/644,755 to Groves filed on Dec. 22, 2006, which is incorporated herein by reference in its entirety. The monitoring system is known as the EA-Tox system in the original patent application and is known commercially as the Greenlight™ Environmental Monitoring System and is marketed by Emilcott of Chatham, N.J., the Assignee of the present application.

FIG. 1 illustrates an EA/TOX monitoring system in accordance with various aspects of the present invention. Environmental air monitoring instruments 10 to 13 are provided. These instruments can monitor a wide variety of environmental and air toxic qualities. For example, they can monitor air quality, water quality and radiation. They can monitor aerosols, dust, particulates, gases, vapors and other components in air. Examples of devices that can be used include dust and aerosol monitors, photo ionization detectors, flame ionization detectors, electrochemical detectors and other detectors of solids, liquids, vapors and gases. These devices may be in a fixed location as part of the system, or they may be mobile personal monitoring devices. The instruments 10 to 13 are in communication with a base station 14.

In accordance with one aspect of the present invention the communication between instruments 10 to 13 and the base station 14 is provided via a wireless link. The communication can be either one-way or two-way between the instruments 10 to 13 and the base station 14. Accordingly, each of the instruments 10 to 13 and the base station 14 typically has a two-way radio device in it. However, communications between instruments 10 to 13 and the base station 14 can also be provided via wired connection or via any other means.

In accordance with another aspect of the present invention a weather instrument 16 can also be provided. The weather instrument measures weather data, such as wind speed, wind direction, temperature, humidity and any other pertinent meteorological data. The weather instrument 16 is in communication with the base station 14, and the communication between the weather instrument 16 and the base station 14 can be provided wirelessly, via a wire connection or by any other communication means.

Instruments 10 to 13 can be located around the perimeter of a site, offsite, and/or within the perimeter of the site. Additional instruments can be provided in the interior of the site or at any location or area designated for monitoring, if desired. Additional instruments can also be provided in the form of personal monitoring devices, which may be worn by employees and/or other personnel present and moving about the site. The site can be a remediation site where environmental clean up is occurring and for which it is important to measure the quality of the air while potentially toxic materials are removed from the site. This site can also be any other construction site, demolition site, remediation site or emergency site. Sufficient instruments are utilized so as to be able to provide adequate coverage at or outside the perimeter of the site, as well as at interior points within the perimeter.

A control unit 15 is in communication with base station 14. The control unit 15 is generally provided in a structure located on the site being monitored, although the control unit 15 can optionally be provided offsite. The communications between the base station 14 and the control unit 15 is can be provided via wired connection, via a wireless interface, such as a radio interface, via a network connection, such as the Internet or an intranet, or via any other suitable communications path.

The control unit 15 includes computers and databases. The control unit 15 receives data from the instruments 10 to 13 and 16 and causes that information be stored in a database and displayed at the control unit 15. The control unit 15 can also provide control of the instruments 10 to 13.

An Internet connection interface 20 is provided to the control unit 15. Thus, various devices such as an alarm 22, another CRT or display 24 or a PDA 26 can be provided. Data from the instruments 10 to 13 and 16 that are stored at the control unit 15 can be displayed on the devices 22, 24 and 26 via the Internet connection 20. The information displayed on the devices 22, 24 and 26 can be real time data as it is obtained from the instruments 10 to 13 or it can be historical data obtained from the database of the control unit 15. The displayed information can also be a combination of both real time and historical data.

A remote annunciator 30 can also be provided and be placed in communication with the control unit 15. The remote annunciator 30 can be a phone, a radio, and/or a PDA. Again, the information displayed at the remote annunciator 30 can be real time data as the control unit 15 obtains such data from the instruments 10 to 13 and 16, or it can be historical data from the database at the control unit 15. Alarms, as they occur from the instruments 10 to 13 can also be provided at the remote annunciator 30.

As aspects of the present invention the following systems and methods are provided herein and will be described further in detail: (1) Measurement of Multiple Ranges of Particle Sizes, (2) Emission Source Identification Using Wind Speed and Direction, and (3) Correlation of Real-Time Imaging Data. All three aspects are concerned with the analysis, reporting and display of the environmental data in question, and are independent of the actual physical methods of obtaining the various field measurements. Such measurements can be made and transmitted by a variety of established, commercially available methods, including the Greenlight™ System.

Measurement of Multiple Ranges of Particle Sizes

As an aspect of the present invention a method and a system are provided for real-time, simultaneous monitoring of multiple ranges of particle size for particulates/aerosol concentration including but not limited to particulates such as dust, soot, silica, asbestos, aerosols, diesel, fuel, metal, mineral, chemical, wood, nano-particles, biological materials, combustion products, burning products or any particulates that can be transported by air, gas and/or liquid and of which a concentration of a presence of a defined range of particle sizes can be measured, and for the mathematical analysis of said data. This may enhance the capabilities of the Greenlight™ System.

For situations in which dust concentration is being monitored, one may operate under a hypothesis that certain types of contaminant sources may have unique, identifiable profiles of particle size distribution depending on the source material and the site operation being performed. Traditional methods of monitoring, analyzing and reporting on airborne dust utilize a single type of particle size measurement for a given installation, typically either Total Particulates or a single specified range, e.g., 0-10 microns (PM 10), 0-5 microns (PM 5), etc. However, it is feasible to simultaneously record and gather field measurements for more than one range of particle sizes at a given location. One may apply any specific field measurement device or technique or combination thereof that is able to gather, to record and/or to analyze more than one range of particle size.

In accordance with an aspect of the present invention, data for more than one range of dust particle size is simultaneously collected, monitored and analyzed. The technique described here is not based on a specific choice of size ranges or on a particular source of material particles. Indeed, the technique is applicable to any practical profile of size ranges, and the requirements of individual site applications may vary in this regard. FIG. 2a shows as an illustrative example, a graph 200, showing a distribution of particle sizes. The scales and numbers in FIG. 2a are examples only, showing the concept of the multi-particle size measurement and display. The number and range of the intervals of size may vary depending on the user-configuration choices and on the selection of field measurement instruments. For instance, in the graph 200, one sees the representation of eleven distinct ranges of particle size, each a band of one micron except for the first and last ranges, which represent, respectively, particles less than one micron in size or greater than 10 microns.

It may be that a first range of particle sizes may be detected by a first measurement instrument and a second range of particle sizes may be detected by a second measurement instrument. The first and the second instrument may be combined in a single embodiment. Such an embodiment having two or more instruments may also be called a measurement instrument or an environmental measurement instrument. Additional measurement instruments, which may measure particle concentrations or other physical phenomena, may also be included in a combination embodiment called a measurement instrument or environmental measurement instrument.

With this data, the enhanced Greenlight™ System may present analyses that distinguish dust levels associated with potentially hazardous sources from those that are impacted by non-hazardous interferences and background emissions. For example, a site remediation activity might involve the excavation and removal of soil with contaminants of a certain particle size. This operation might also employ diesel powered vehicles, for which the emissions are not a source of interest for regulatory compliance. Traditional methods might confuse the two sources by monitoring for Total Particulates, while the method proposed here would distinguish the diesel emissions from larger dust particles from the soil. The term dust herein should be considered in its broadest interpretation as a concentration of particles in air/gas or liquid.

Figure 2B:
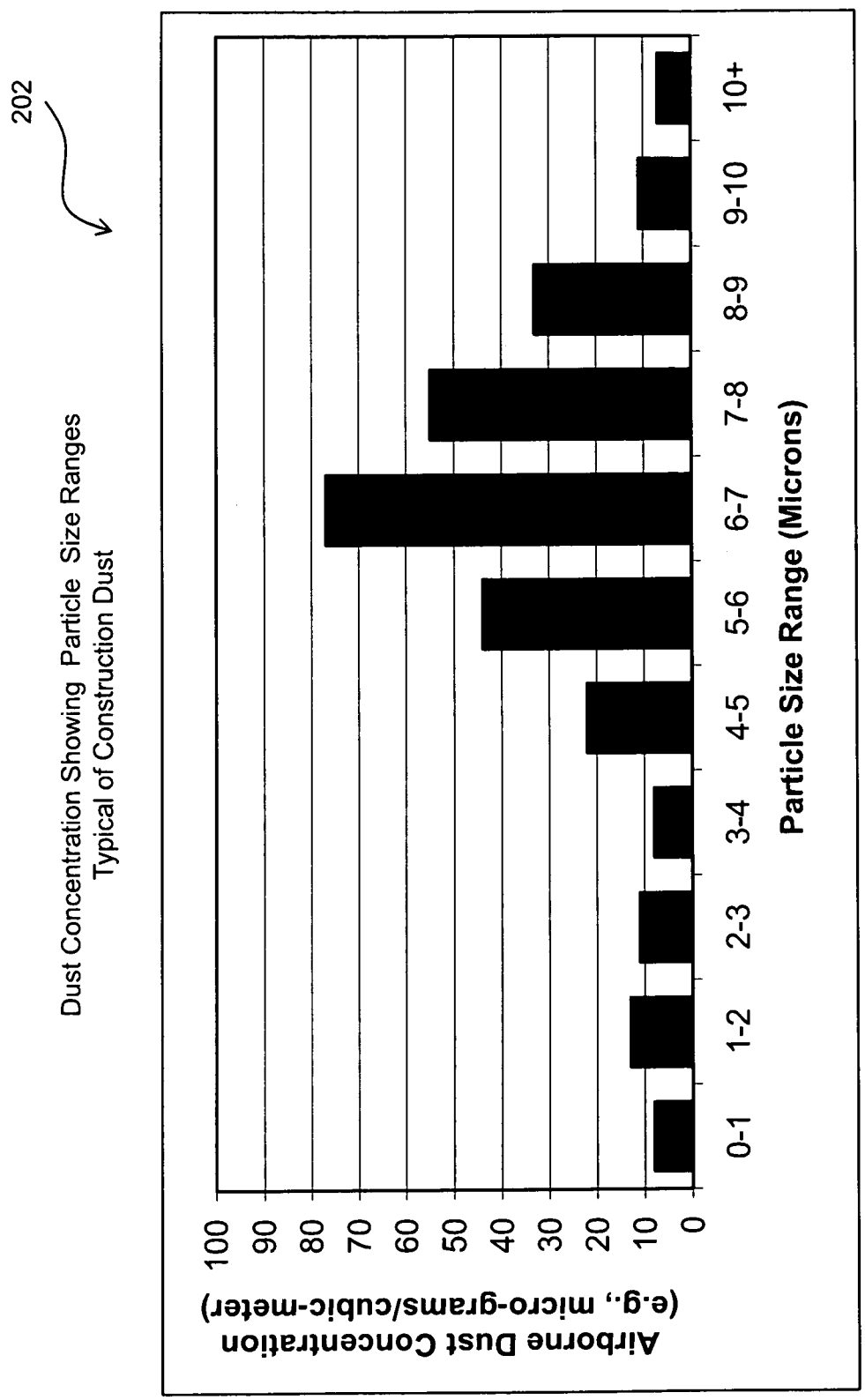
Figure 2C:
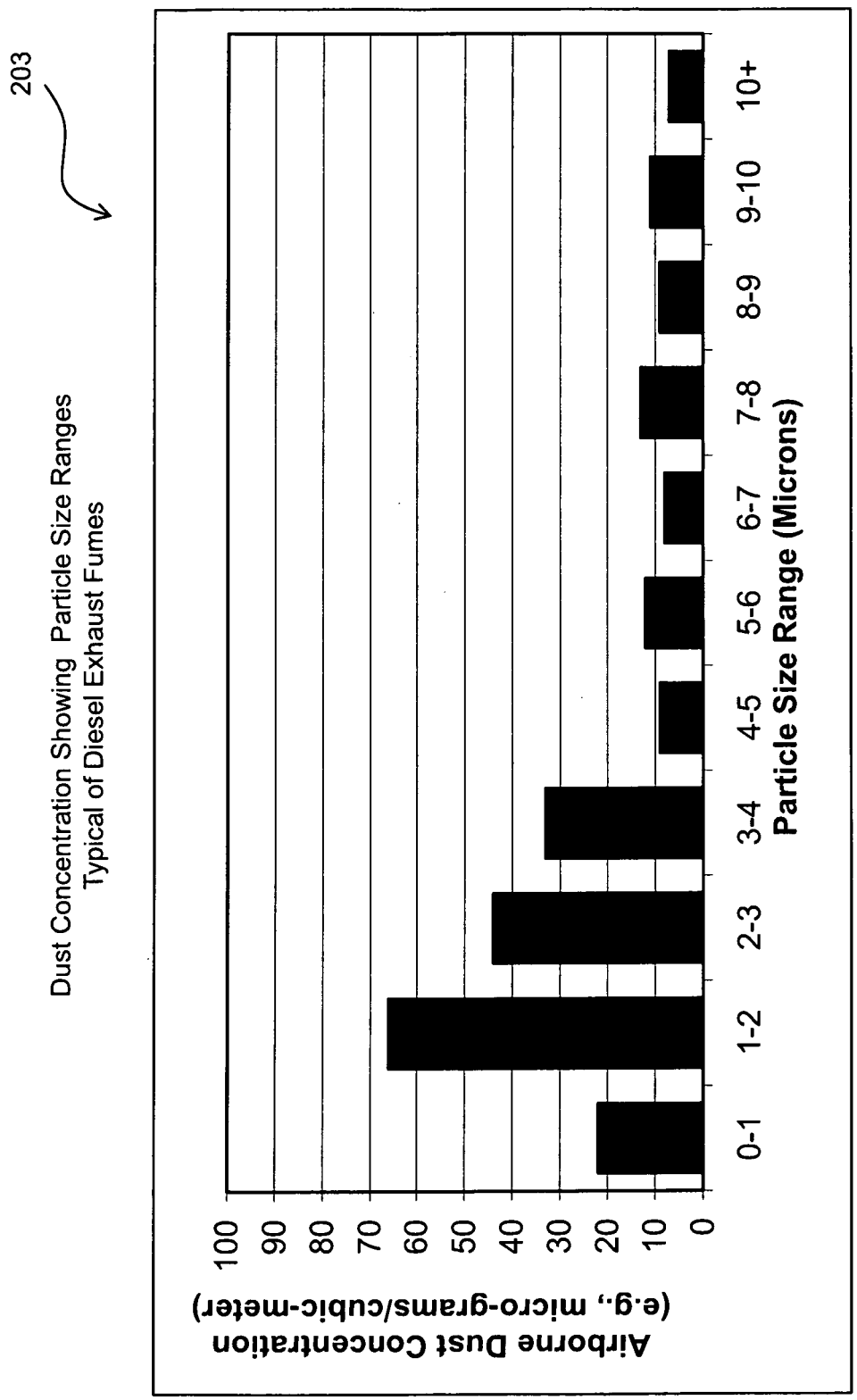
Figure 2D:
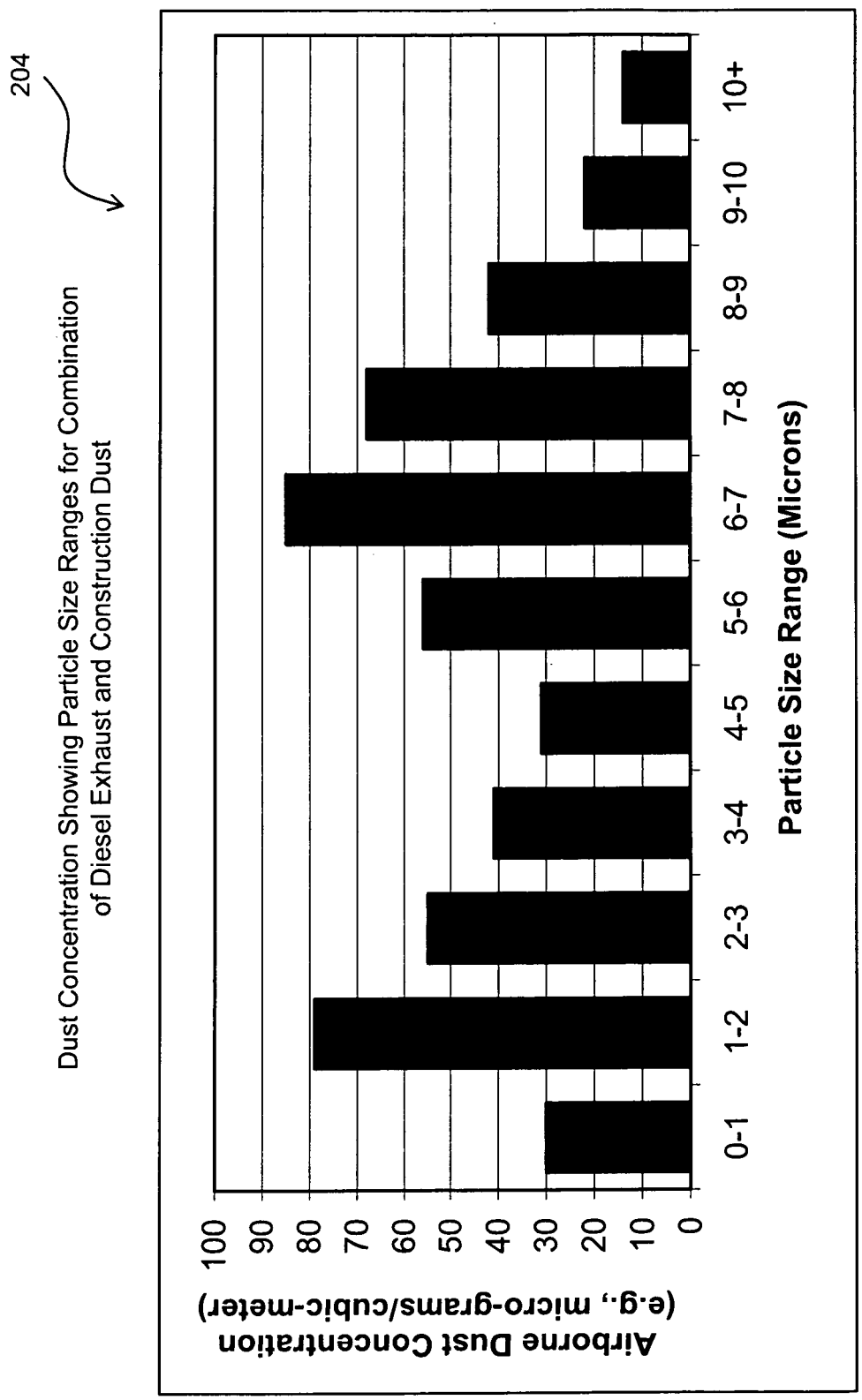

As an illustrative example one may expand the above example. For instance during an excavation particles or ordinary dust may be released into the atmosphere that are distributed over a broad spectrum of particle sizes but with greatest concentrations in a narrow range of sizes. FIG. 2b graph 202 presents this example graphically, showing the greatest concentration of particles in the size range of 6 to 7 microns. Furthermore, a diesel engine working on the site releases exhaust particles predominantly in different narrow range of particle sizes. FIG. 2c graph 203 presents this example graphically, showing the greatest concentration of particles in the size range of 1 to 2 microns. FIG. 2d graph 204 presents the superimposition of these two examples, as might be characteristic of site conditions if the construction dust and diesel exhaust were simultaneously present. Assume that at a certain moment an increase is detected in the concentration of particles in the second range, exceeding an alert or alarm level. A system may be instructed, for instance based on the knowledge of existing, suspected or possible sources of generating those particles, that only an alert or alarm may be provided if also the concentration of particles in the first range of sizes also has exceeded a preset concentration level.

As a further aspect of the present invention one may store in a database a distribution of concentrations of different ranges of particle sizes related to an occurrence of a material in the environment as a profile of the presence of that material.

The detectors and other instruments may be situated on a field in the same manner as depicted in the earlier cited patent application Ser. No. 11/644,755. The location of all detectors will be known to a system in terms of geometric coordinates that may be superimposed on a map of the site in question.

The dust concentration measurements for multiple particle-size ranges may be transmitted to a Control Unit in a manner similar to that of other data being gathered by the system as described in the earlier cited U.S. patent application Ser. No. 11/644,755. The measurement devices may be configured as one or more of the optional detector types that can be configured on the system as disclosed in the earlier cited U.S. patent application Ser. No. 11/644,755 for a given site installation. Such configuration options may be created based on the performance characteristics of one or more commercially available products suitable for this application.

The dust concentration measurements may be gathered in real-time and may be stored in a database at the Control Unit, along with data from the other types of field instruments, if any. All data items may be stored with a time-stamp (date and time-of-day to the second) and with the geometric site coordinates of the instrument in question.

In accordance with a further aspect of the present invention the data for particle or dust concentration may be analyzed by software to create a mapping of the site in question which may be multi-layered, so as to identify the geometric coordinates of each measurement for each range of particle size being monitored. Such a mapping may be shown on a display, and it may be a scale map of the site, an aerial photograph, or a schematic diagram reflecting the site being monitored. The locations of the measurement instruments may be identified on the displayed map. Such identification may be by an icon, a shape, a number or any other element that identifies a measurement instrument. Measured concentrations of a range of monitored particle sizes may also be displayed. Such concentration display may be in numbers, for instance accompanied by a time stamp. Concentration display may also be differentiated in size, color shape or any other property that may differentiate a display from another display. This allows a viewer to distinguish between classes of sizes, concentrations and time stamps. One may also be able to display concentrations based on time-stamp, location, level, change in level, range of size, criticality to site operations, or any other property that is deemed being of relevance.

In a further embodiment one may display measurements only if they meet certain criteria, such as pre-set alert or alarm levels.

A mapping may also be a virtual mapping. This means that all measurement data have their properties assigned and stored in a database in a searchable manner. Accordingly, all data can be searched, sorted, selected and, if required, displayed based on those properties, which may include but is not limited to location coordinates, range of particle size, concentration, time stamp, and alert or alarm level among others. In a further embodiment the properties of measurements may be associated with other measurements, which may include weather measurements, chemical measurements, and other measurements of potential physical hazards, such as noise and radiation.

Furthermore, in accordance with yet a further aspect of the present invention the analysis by the software may incorporate the threshold limits of the different particle sizes of interest, as established by the site owner and/or regulatory compliance requirements. This will allow an alarm notification to be based on specific particle size and on geometric location of the measurement. This, in turn, may assist in the management of site operations by enhancing the traditional alarm notification process distinguishing emission levels by narrow ranges of particle size.

To facilitate identification of particles and concentrations of interest one may store identifiable profiles of certain environmental measurements in a database. For instance materials of interest at a site may occur in aerosols in a certain distribution or concentration of particle sizes. Particles of a certain size may for instance occur from a contaminant that is being removed from a site. Particles of that size may also occur for instance in diesel exhaust from traffic. Occurrence or absence of particles of a different size may indicate that what is being measured is a diesel exhaust rather than a contaminant of interest. One may call this differentiation by analysis of the identifiable profiles. One may build a database of such profiles, either from first principles or from empirical data collected from the site in question or from previous measurements at other sites. Such data may include re-use of a known distribution of particle sizes related to a material or contaminant of interest. One may further associate these identifiable profiles in the database with distributions or concentrations that are related to a known situation or type of source. Such situations may, in some cases, be associated with distributions or concentrations that can be considered as background levels and/or non-hazardous situations. One may also assign alerts or alarms to certain levels of concentration of particles. One may also assign alerts or alarms to changes in concentrations.

Figure 3:
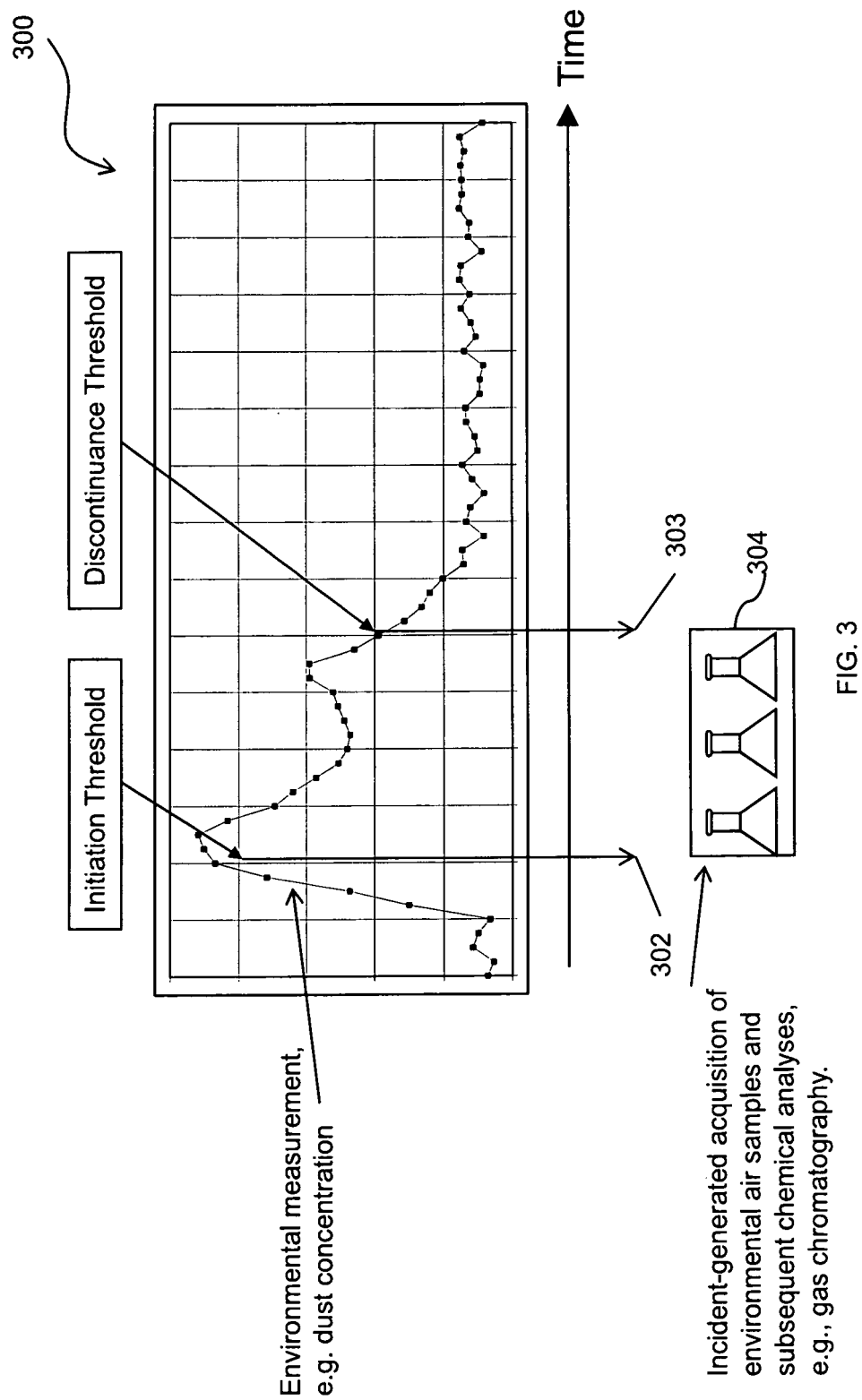
FIG. 3 illustrates another embodiment of an environmental monitoring system in accordance with one aspect of the present invention.

There are situations where measured particle size distributions of a material may indicate a situation of concern and an alert may be provided to a user or a human operator to assess a condition. Alternatively, a situation may occur wherein the measured distribution of particles may be cause for concern but not sufficient for issuing an alert. In such a situation an automatic analysis may be initiated, for instance a chemical analysis performed by an instrument, that will provide a greater certainty of the properties and distributions of the material of interest. Such an instrument may or may not perform in real-time or operate continuously. In that case the chemical analysis may be initiated based on a specified concentration of particles of a certain size or range of sizes. Such an analysis may also be triggered on a trend of increasing concentration of certain particle sizes. FIG. 3 graph 300 illustrates the initiation of such a supplementary chemical analysis when a threshold concentration is reached. A system may be instructed to initiate one or more such analyses when triggered, depending in the site-specific needs for environmental monitoring. Such a trigger may occur at a preset threshold level, such as a level 302 as shown in FIG. 3. A chemical analysis, for instance by an analysis apparatus 304 may be able to infer the presence or absence of possible occurrences of interest. This may lead to additional action or intervention as part of site operations, for example, suspending excavation areas activities or implementation of environmental controls. One a detected concentration of a certain particle size has crossed a threshold level 303 so that the concentration does no longer exceed the threshold 303, the analysis 304 may be stopped or suspended.

Figure 4:
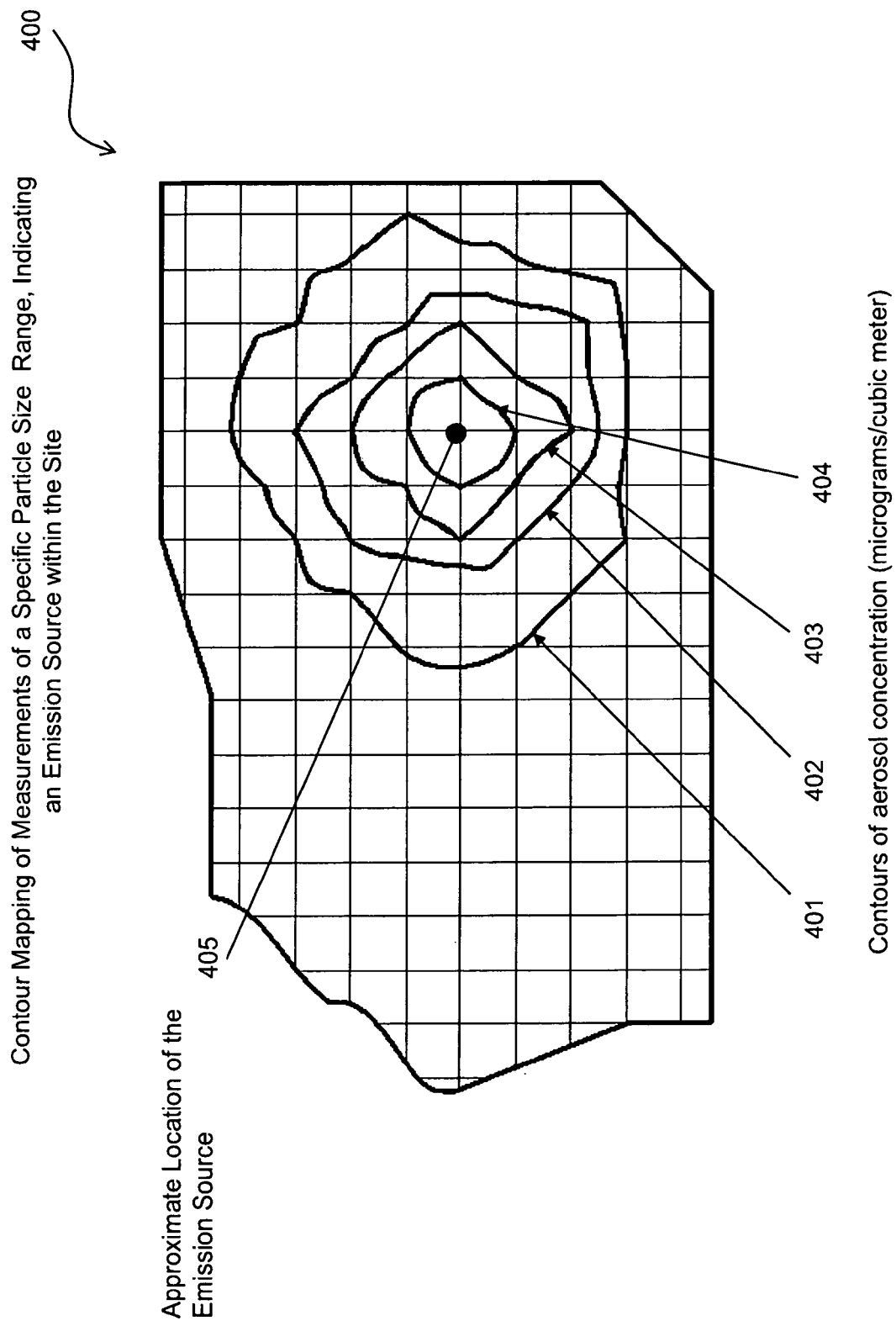
FIGS. 4 and 5 illustrate in diagram a concentration contour map in accordance with an aspect of the present invention.

In accordance with yet a further aspect of the present invention, the analyses, described above, by software may be presented to the end-user in the form of map views of the site. Such views may include graphic representation of contours of dust concentration by particle size. It may also include highlighting areas in a map as an area of concern. A system may be instructed to utilize this capability to help determine if sources of emission of substances of interest are located within or external to the site in question. FIG. 4 presents a graphical example of this technique in which the source is indicated to be within the site. This technique is shown as a map 400 in FIG. 4. Herein 401, 402, 403 and 404 are contours indicating areas of different concentration of particle sizes, for instance as contours of aerosol concentration (micrograms/cubic meter). Contours 401 to 402 to 403 to 404 show an increasing concentration. Point 405 may be determined by the system as being the location of the source of the particles.

Figure 5:
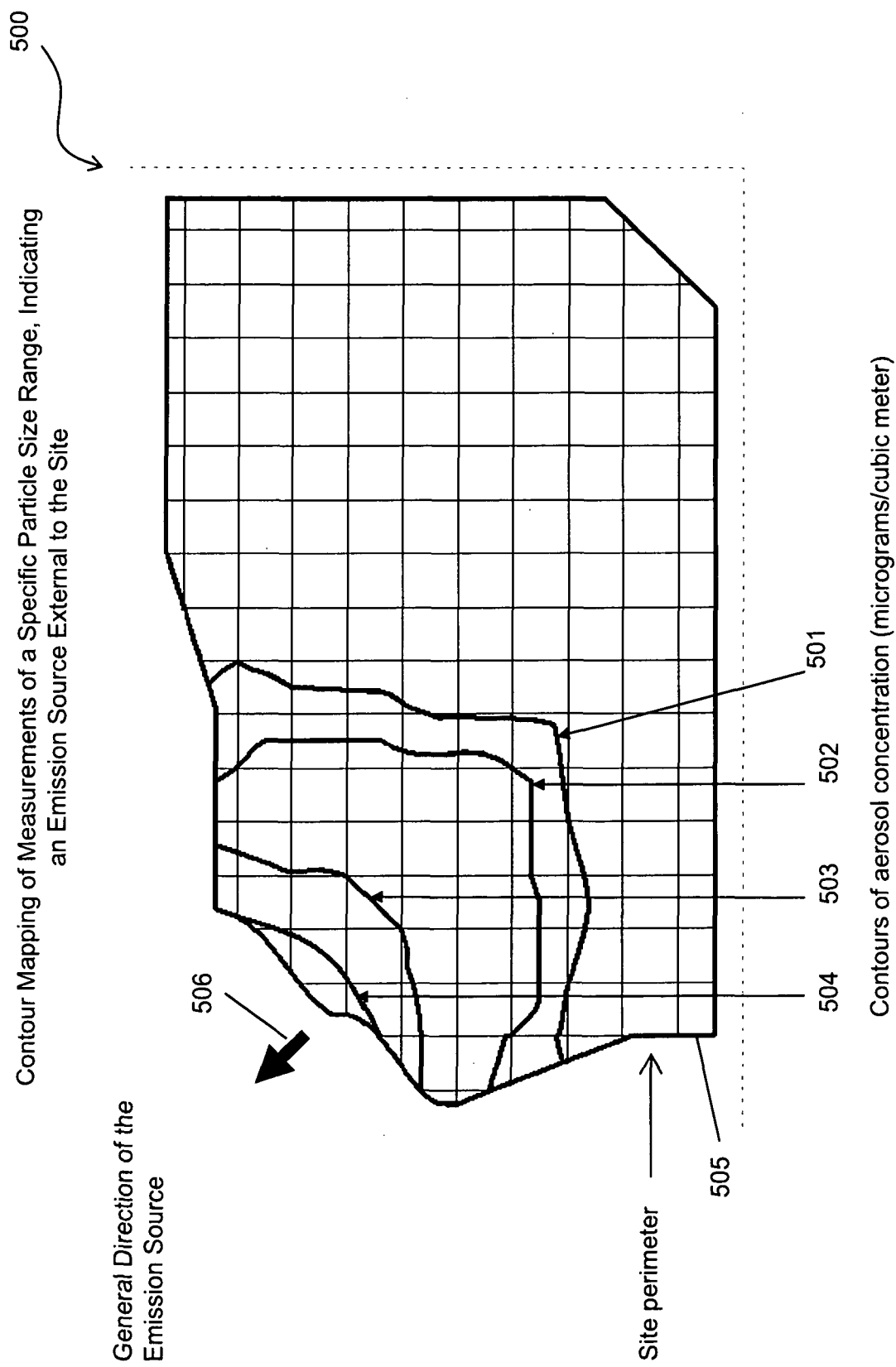

The example of FIG. 4 illustrates the concept of the map with one or more contours. It is also possible to overlay contours of concentrations of different particle sizes. This may for instance show different sources of different particles. It may also show that certain particles have a single and perhaps fairly narrow concentration, thus showing that a source may not be located within an area represented by a displayed map. FIG. 5 presents a graphical example of a map 500 of the technique in which the source is indicated to be external to the perimeter 505 of the site in question. Herein contours 501, 502, 503 and 504 show again an increasing concentration. It may be determined that a source of particles may be located in the direction 506. It is also possible that no gradient in contours exits, but that the concentration is of such a level that it may be determined that no source of particles is present within the perimeter, or that such a source if it is within the perimeter is not of significance.

In a further embodiment one may provide a computing device with the data related to the contours as shown in FIGS. 4 and 5 to determine or to estimate a most likely location of the highest concentration of materials within a first and/or a second range of particles.

In a further embodiment one may provide an estimation of a location of a source of material based on contours of measured data and of measured wind direction and strength as will be provided later herein.

The instruments, controllers and other components and apparatus are part of a monitoring system. The monitoring system has at least one computing device. The computing device has a memory or memory device enabled to store and retrieve data and instructions and a processor, the processor enabled to retrieve and execute instructions retrieved from memory and operate on data retrieved from the memory or from a data storage medium. Instructions may be combined into a software program that may be executed by the processor. The computer program may be stored on a data storage medium which may be but is not limited to a magnetic disk, a magnetic tape, an optical disk or an electronic storage medium which may be a flash memory.

Emission Source Identification Using Wind Speed and Direction

In accordance with another aspect of the present invention an environmental measurement system is provided for measuring particle sizes and for real-time monitoring of wind speed and wind direction at multiple stations at the perimeter of the site. In accordance with a further aspect of the present invention the system may also perform real-time monitoring of other meteorological data, e.g., temperature, humidity, and precipitation. In accordance with a further aspect of the present invention the system may also perform mathematical analysis of data, along with other environmental data collected by the system, for instance for the purpose of discerning a location of a source of emission. One or more instruments at a location may be combined in a station. A station may be equipped with communication equipment, which may be wired or wireless equipment, which allows a station to transmit collected measurement data and/or processed data to be transmitted to a server or a controller which is enabled to receive and store the received data. Instruments may also be equipped individually with communication equipment to transmit data to a base station or a controller.

In a further embodiment, an environmental measurement system may comprise one or more instruments for measuring wind direction and wind speed and one or more instruments that measure an environmental parameter, such as a presence and/or a concentration of a material in the atmosphere wherein at least one instrument does not determine a particle size. Such materials may include but are not limited to hydrocarbons, chlorine and chlorine compounds, volatile organic compounds (VOC); benzene, toluene, ethylbenzene, and xylenes (BTEX); ethane, propane, butane, butadiene, hexane, toluene, nitrous oxides (NOx); sulfur and sulfur compounds including sulfur dioxide and hydrogen sulfide, Ozone, Carbon dioxide, carbon monoxide; semi-volatile organic compounds; naphthalene; dioxins, polychlorinated biphenyls or any other material of which a presence and/or a concentration can be measured in an atmosphere.

In yet a further embodiment, an environmental measurement system may comprise one or more instruments that determine a presence and/or a concentration of a material in the soil or in the ground water. Such materials may include but are not limited to hydrocarbons, chlorine and chlorine compounds, volatile organic compounds (VOC); benzene, toluene, ethylbenzene, and xylenes (BTEX); semi-volatile organic compounds; naphthalene; dioxins, ethane, propane, butane, butadiene, hexane, toluene, nitrous oxides (NOx); sulfur and sulfur compounds including sulfur dioxide and hydrogen sulfide, Ozone, Carbon dioxide, carbon monoxide, dioxins, polychlorinated biphenyls or any other material of which a presence and/or a concentration can be measured in a soil or in groundwater.

In yet a further embodiment the environmental measurement system may also comprise a device, which may be a computer device with correlation software that is enabled to correlate a presence or a concentration of a material that is measured or determined in a first location, with a concentration or a presence of a material measured in a second location and/or in a third location. For instance, a second location may be upwind from a first location and a third location may be upwind from the second location. It may be determined that the first, the second and the third location are all in a same wind stream. By determining for instance concentration differences of a material in the atmosphere at the first, the second and the third location one may determine that the downwind concentration in the first location is much higher than in the second and the third location. The computer device with the appropriate software may analyze material concentrations along a wind stream pattern and may determine that material was released into the atmosphere from a location on or downwind from the second location.

In a further embodiment one may determine a presence or a concentration of the material in the soil or ground water at or close to the first, second and/or third location. A measurement of a high or a higher concentration of the material in the soil or ground water at the second location may indicate that the second location is a location of a potential source of the material to become airborne and enter the atmosphere.

Figure 6:
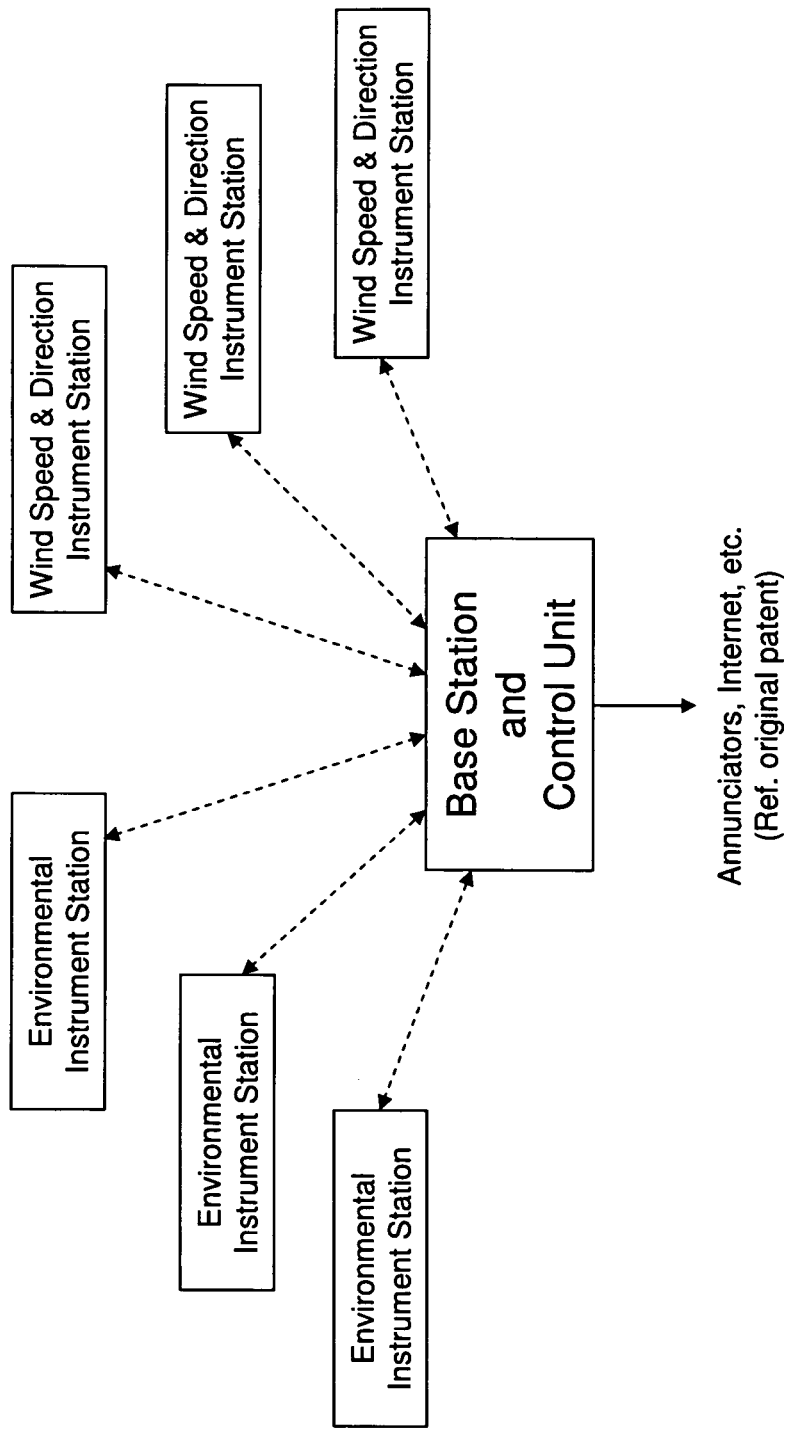
FIG. 6 illustrates in diagram an environmental monitoring system in accordance with an aspect of the present invention.

In accordance with a further aspect of the present invention a measurement station can be in one physical housing or enclosure to contain a plurality of detectors of the system, such as the detectors or measurement instruments for measuring dust and vapor; or they could be housed in separate enclosures near the other types of detectors. A possible architecture of a system applying weather related instruments is shown in diagram in FIG. 6. Conceptually, in terms of data acquisition, the wind measurement stations are distinct from other environmental detectors. The number of wind measurement stations deployed for a given installation will vary depending on the size and topology of the site, whether any significant physical obstructions exist on the site, and the number of other types of detectors required for the environmental monitoring to be done.

The location of all detectors will be known to the environmental measurement system in terms of geometric coordinates superimposed on, for instance, a map of the site in question. An illustrative diagram of such a map 700 is provided in FIG. 7. Herein a field station with Wind speed and wind direction detectors, and optionally other meteorological detectors is indicated by W. A field station with other environmental detectors, e.g., dust, vapor, humidity, etc. is indicated by an E.

The wind speed and wind direction measurements will be transmitted to the Control Unit in a manner similar to that of other data being gathered by the system as disclosed in system as described in the earlier cited U.S. patent application Ser. No. 11/644,755. The wind measurement devices will be configured as one or more of the optional detector types that can be configured on the system for a given site installation. Wind measurement devices as well as other weather related devices such as thermometers and humidity detectors are commercially available and may be included when they are required.

The wind speed and wind direction measurements may be gathered in real-time and stored in a database at the Control Unit, along with data from the other types of field instruments. All data items will be stored with a time-stamp (date and time-of-day to the second) and with the geometric site coordinates of the instrument in question.

Figure 8A:
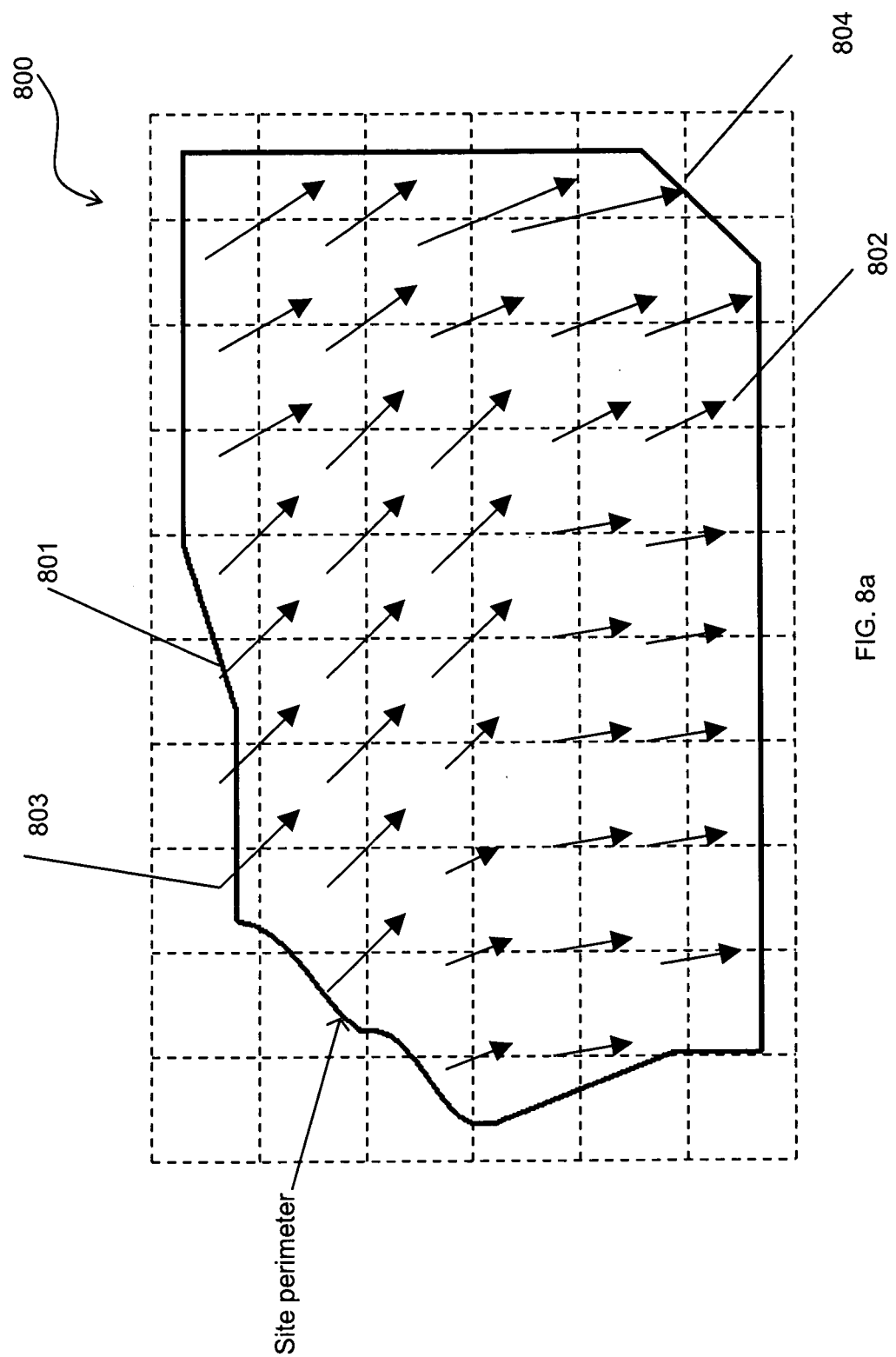

The collected data for wind speed and wind direction may be analyzed by the environmental monitoring system by a computer program. A computer program may also be used to create a mathematical model of the wind movements across the site from the collected data. This model may quantitatively describe the wind-induced flux of the air entering, moving across and leaving the site. This model may be derived from two-dimensional interpolation and/or other analysis of the wind speed and wind direction measurements. The calculated model may be displayed and superimposed on a map 800 of the site as shown in FIG. 8*a*. For instance, arrows 801, 802, 803 and 804 indicate a wind vector with a magnitude and a direction. FIG. 8*b* presents a variation on this capability in that the mathematical model map 810 of the wind movements may be instructed to account for the effects of buildings 811 and/or other obstacles present on the site in question.

Furthermore, analysis by environmental monitoring system software may apply or incorporate the related environmental data measurements for the site, e.g., the concentrations of particles with certain ranges of sizes of the substances of interest being monitored. A database of the system may store a library of substances of interest based on distinct profiles of materials. These profiles may be based on the measured environmental data. These profiles may also be correlated with the mathematical model of wind-induced flux on the site based on measured wind data.

Figure 8C:
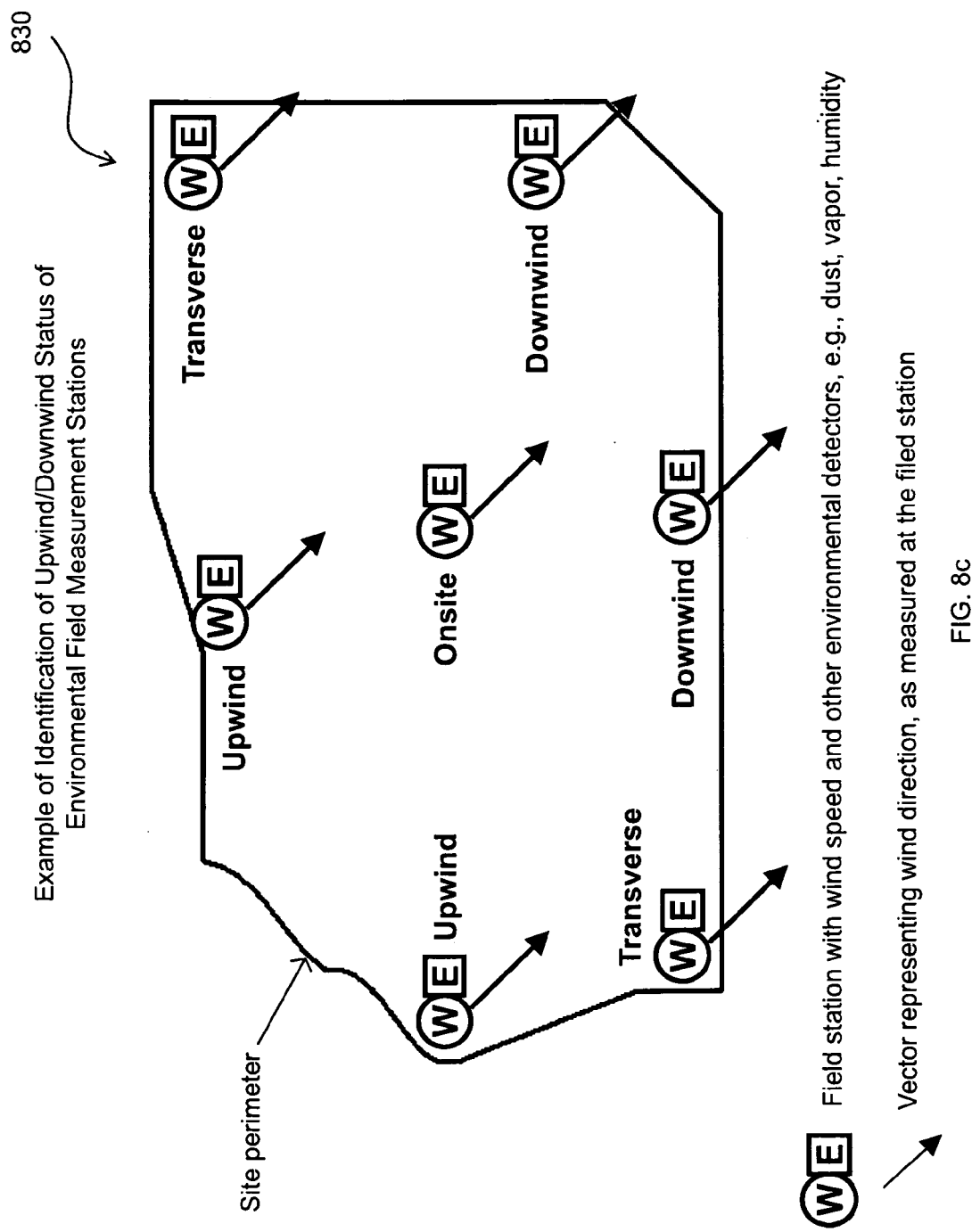
FIG. 8c illustrates another embodiment of an environmental monitoring system in accordance with an aspect of the present invention.

By mapping these environmental measurements onto the mathematical flux model, the software analysis can infer the location(s) of the source(s) of any substances of interest. Specifically, this analysis may determine whether the substances of interest are originating outside the perimeter of the site but being carried onto the site by the wind (upwind source), originating within the site (onsite source), leaving the site (downwind), or not having a material effect entering or leaving the site due to the combination of location and wind direction (transverse). In FIG. 8*c* map 830 presents a schematic example of these concepts, depicting the location of field measurement stations indicated by an E and the wind direction measured at each station W, and labeling the upwind/downwind status at each station. In addition, the analysis will provide a quantified estimate of the location of the source(s) of such substances, based on the known geometric coordinates of the site. This will be accomplished by accounting for, and subtracting, background or upwind emissions so as to eliminate interferences and better discern the source and magnitude of significant environmental emissions. In accordance with a further aspect of the present invention, one may determine, based on a measurement of a presence and/or a concentration, and/or a concentration of a particle size in the atmosphere, combined with a measurement of a wind speed and a wind direction, if a source of emission of material in on the site or potentially outside the site. To that end, one may use to monitor and evaluate airborne concentrations and windborne movements which may include but is not limited to one or more of the following: total concentration of volatile organic compounds (VOC); total concentration of benzene, toluene, ethylbenzene, and xylenes (BTEX); semi-volatile organic compounds; naphthalene; Concentration of specific individual VOCs, such as ethane, propane, butene, butadiene, hexane, benzene, toluene, ethylbenzene, xylenes, etc.; Nitrous oxides (NOx); Sulfur and other sulfur compounds, such as sulfur dioxide and hydrogen sulfide; Ozone; Carbon dioxide; Carbon monoxide; etc.

Furthermore, the analysis by the environmental monitoring system software may incorporate the threshold limits of the substances of interest, as established by the site owner and/or regulatory compliance requirements. This will assist in the management of site operations by enhancing the traditional alarm notification process to include knowledge of the source(s) of undesirable emission levels.

One may create a database having relevant information on material and material properties, including concentrations of particles in different ranges of size. Such a database may also contain alerts, indicating at what level of concentrations an alert should be issued. It may be known that at certain wind directions, or at a certain wind speed or other weather conditions, certain concentrations of one or more materials warrant an alert. These concentrations may not warrant an alert at other weather conditions. For instance, water vapor in the form of fog has a particle size distribution that may be similar to environmental substances of interest. In this case, the use of measured humidity data may allow the database to distinguish between benign and potentially hazardous situations. Separately, for instance, high temperatures and/or strong winds towards a neighborhood downwind from a site may require adjustments to site operations. All such known conditions may be stored in a database.

FIGS. 8*a* and 8*b* show maps that may be called wind maps. Using a mathematical model, a windmap may be generated from wind measurements from a limited number of locations. Wind characteristics such as strength and direction at locations not having a wind measurement device may be determined from processing measured wind data in a mathematical model, thus enabling the generation of a windmap covering a site that is being monitored. In addition to providing calculated wind characteristics, a computer device with the appropriate software can also provide estimated concentrations of a material at certain locations based on measured concentrations at locations with measured concentrations. In one embodiment one may apply common interpolation methods between two measurement points. One interpolation method that may be applied is a linear interpolation; another interpolation method is polynomial interpolation; yet another method is spline interpolation; or one may use any other interpolation method that allows the generation of a windmap with interpolated wind characteristics and material concentrations or any other interpolated characteristic that can be derived from measured data.

One manner of displaying measured and/or interpolated characteristics on a map that is by applying streamlines or pathlines of the wind. One may then related to locations on a pathline or a streamline display for instance a concentration of a material. A windmap created in the above matter then shows how a concentration of a material may change along a pathline or a streamline. When a concentration at the beginning of a pathline or streamline is low, and it is consistently high further down a pathline or streamline, it should be clear that the wind has picked up material along its way. If such pathline or streamline travels along a site that is being monitored it is reasonable to conclude that the wind has picked up material along its travel over the site. If down a pathline or a streamline the concentration of a material has not increased in a significant manner, it is reasonable to assume that the material was brought in by the wind from a source external to the site.

Relations between wind and material concentrations can be empirically checked, and related profiles can be stored in a database. One may thus correlate a measured and/or calculated wind map with the stored empirical profile, and derive a conclusion on material sources and material transportation by wind that is correlated to empirical data. Such a conclusion may be provided as an estimate, including a probability of certainty of a conclusion. When there is a strong wind and wind leaving a site has a lower or about the same concentration of a material compared to wind entering the site, then there is a high probability that the material carried by the wind originates from outside the site. When there is a moderate wind and the concentration of a material in wind leaving the site is considerably higher than wind entering the site, there is a high probability of the material originating from the site. The system may check material concentrations in the wind against a material profile in a database. The system may then conclude with a certain probability that a source of diesel exhaust may be at or near the site. Accordingly, the system may provide an alert to check for a diesel exhaust source at or near the site. Such an alert may be accompanied with a probability of a most likely location. It may also contain additional estimates of probable materials and their location. An operator or a program in the system may then check against for instance expected or likely or possible materials at the site.

The illustrative wind maps of FIG. 8a and FIG. 8b demonstrate that particles entering a site carried by the wind may not leave the site at a point and in a direction derived from a straight line drawn from the point of entry. In several cases one would like to determine a concentration of a material entering a site at a certain point and the concentration of the material leaving the site at a corresponding point. One may for instance want to determine if the concentration at a point of exit was lower than at the point of entry, unchanged or perhaps higher. A significantly higher concentration may be a reason for an alert. In accordance with an aspect of the present invention entry points and exit points of a site for wind carried particles can be determined and may be associated with measured concentrations of particles at those points. Based on predetermined alerts and measured wind speeds and measured concentrations one may determine if a measured concentration of a material at a wind exit point of a site was caused from material gathered from the site. For instance one may determine that a high concentration of material was already present at the entry point and that a high measured concentration at an exit point was not caused by material and/or activities at the site.

A wind map provided herein as an aspect of the present invention may be a displayed map such as a topographic map, or a diagram of a map. A map herein may also be a virtual map or a digital map. A digital or virtual map is a set of data, wherein locations are represented by coordinates or data and wherein objects, landmarks and the like, are associated with the coordinates in a database. In a wind map, locations are associated with a wind speed and a wind magnitude. A virtual or digital map can be applied to provide a displayed map.

In accordance with a further aspect of the present invention the provided methods of analyzing data collected from instruments, processing these data and assessing data against data stored in a database may be executed by a computer program.

The analyses, described above, by environmental monitoring system software may be presented to the end-user in the form of map views of the site. Such a view may be generated in real-time or close to real-time and may be provided on a display. Such views may include graphic representation of contours of wind speed and wind direction, as well as the estimated source location of emissions from substances of interest.

The system as provided as an aspect of the present invention is able to collect, process and display a significant amount of data. It may not be in the best interest of a human user to have to review or assess all data at the same time. The system in accordance with a further aspect of the present invention is provided with an input device that may control the display of data. Such an input device may be a key-board or a mouse, which may control actions by the system and data displayed on a display. For instance, a human user may select for instance with a pointer controlled by a mouse in a map which is displayed on a display an area or a location for which additional information may be displayed by the system. For instance clicking on a location may provide data of wind direction and magnitude. It may also provide concentrations of measured particles or any other information that is associated with that location.

Clicking on a location may also activate a second menu from which information displays may be selected. Or clicking on a location in a map may activate icons or other indicators that when activated provide more relevant data. A location may be highlighted by the system to indicate that an alert was issued.

One may also click on two locations on a map. This may display at both locations a wind vector and one or more concentrations of material. A differential of material concentration of the two locations may also be displayed. One may also click on a location and possibly on a menu item and a related location may be highlighted. A related location may for instance be an upwind location. The upwind location may be the location from which the wind passing through the location originated. A related location may also be a downwind location where the wind going through the present location will pass through later. A related location may also be a location having the same wind direction or having the same wind magnitude or both. A related location may also be a location having the same or about the same concentration of a material. One may also cause by activating a location on a map activate a streamline or a pathline of wind going through the location and display if required selectively data from measurements performed or related to other locations on a streamline. Other related locations may be identified and may also be highlighted, selectively if so desired.

In a further embodiment of the present invention, a program based on data gathered from a site may calculate a wind direction and magnitude and a material concentration at a location. In a further embodiment a display may not provide such calculated data until an operator clicks on a specific location in a map, after which wind and/or material concentration data may be displayed.

In yet a further embodiment, locations on a map may be clicked and may be marked for close monitoring. For instance when the wind picks up in speed or is expected to increase in force, one may want to watch certain locations more closely. One may identify such locations on a displayed map and for instance with the help of a menu provide a command to display data related to certain locations.

In yet a further embodiment one may provide "known sources of particles on the site" to the environmental system. For instance, it may be known that during working hours, equipment using diesel engines will be active at the site. A program using a database having a profile of diesel exhaust particles may decide that data provided through a wind map and matching diesel particles originate from equipment working at the site. In a further embodiment, one may provide equipment with diesel engines with mobile positioning equipment such as GPS. If high particle concentrations, matching diesel particles, are detected, but the particle concentration is only higher on a windpath with a piece of equipment in it, it is reasonable to assume that the equipment is the source. One may cover different scenarios for such an embodiment, including scenarios that apply wind force. In a further embodiment one may provide data if an engine is active.

Many other and different ways of activating the display of data in a graphical or character or symbol based manner are possible and are fully contemplated as an aspect of the present invention. The above is merely an illustration of the different ways data may be displayed. It should be clear that data may be displayed selectively. This may take place as consequence of an action by a user. It may also be as the result of an action by the system. For instance, if an urgent alert is generated by the system, it may stop displaying less relevant data and provide only the most urgent or relevant information.

Correlation of Real-Time Imaging Data

As a further aspect of the present invention an enhancement of an environmental monitoring system is provided for acquisition of real-time images at multiple locations on and near the site under observation, and for the correlation of said images to the other environmental data collected at the site by the environmental monitoring system.

Visual observation of site activities and conditions can greatly enhance the ability of site personnel to draw conclusions about the state of site operations, possibly determine the source of emissions, and make operational decisions.

The approach may be two-fold:
(1) To collect image data from dedicated real-time cameras and/or other imaging sources and store said data in a database on the environmental monitoring system's Control Unit. This technique can be used in real-time, to display images to site personnel, and separately for after-the-fact analysis of incidents.
(2) To accept image data from other source systems, provided that such data has a time-stamp in suitable format to be used by the environmental monitoring system. This technique will be restricted to after-the-fact analysis of incidents.

The recording and displaying of images is not limited to specific equipment or formats for obtaining and recording images. They may include still images, continuous video images, and enhanced detection techniques such as infra-red or thermal imaging. Various configuration options for the environmental monitoring system may be provided based on the performance characteristics of one or more commercially available products suitable for this application.

Figure 9:
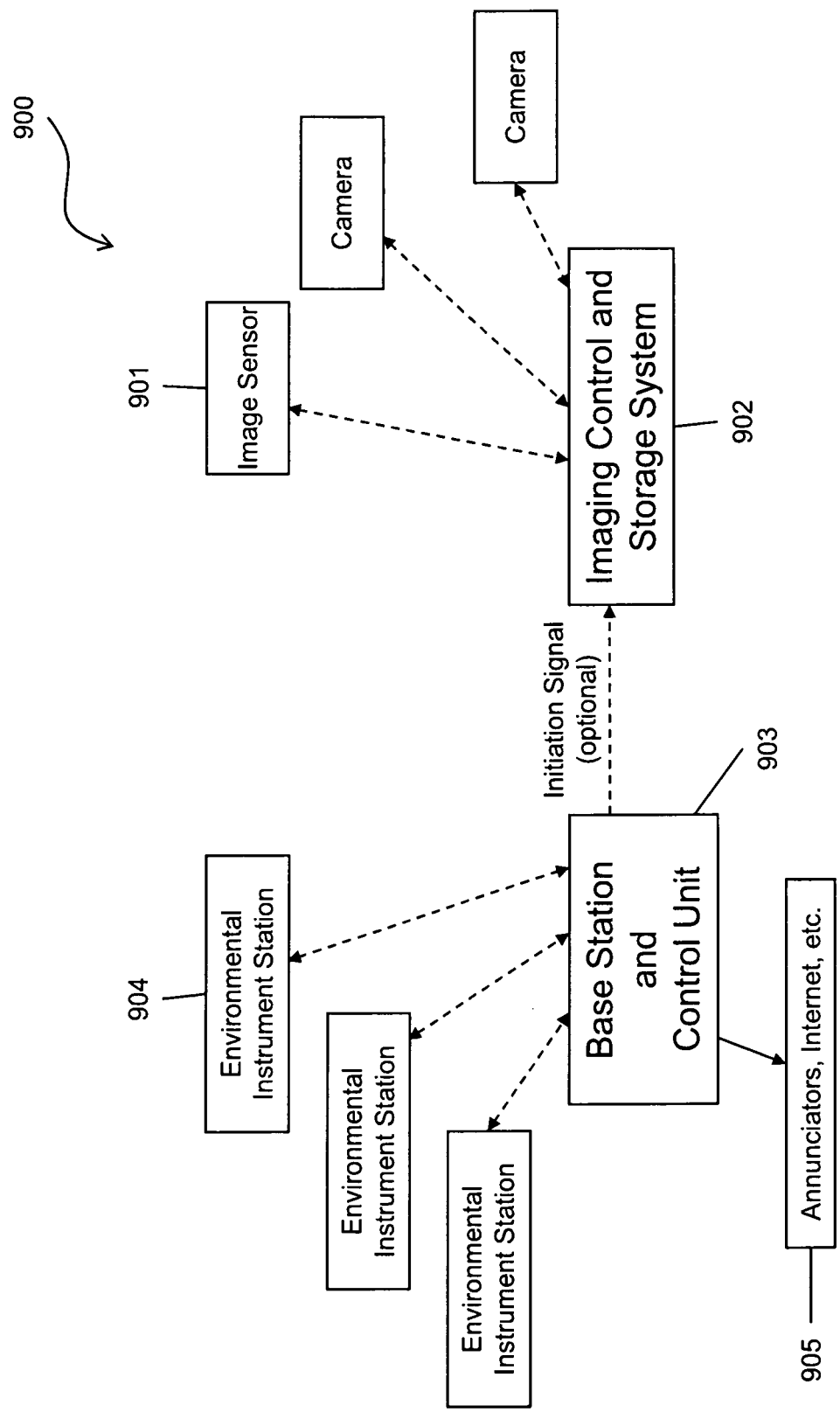
FIG. 9 illustrates in diagram an environmental system in accordance with an aspect of the present invention.

FIG. 9 shows a diagram of an environmental monitoring system 900 in accordance with an aspect of the present invention. The system has one or more image sensors 901, which may be a camera, an infrared sensor or a thermal sensor or any other sensor by which an image may be created. A sensor is controlled by an Imaging Control and Storage System 902 which may be available as commercial products. System 902 controls the image sensors and stores recorded images. Imaging Control and Storage System itself is controlled by the environmental monitoring system Control Unit 903. Unit 903 also controls and receives data from other Environmental Instrument Stations 904, which includes at least a measurement instrument for measuring a concentration of a particle. It may also contain an instrument for weather conditions, including wind speed and direction, or any other instrument that is useful for monitoring environmental conditions. The unit 903 is also connected to an earlier disclosed annunciator 905.

Figure 10:
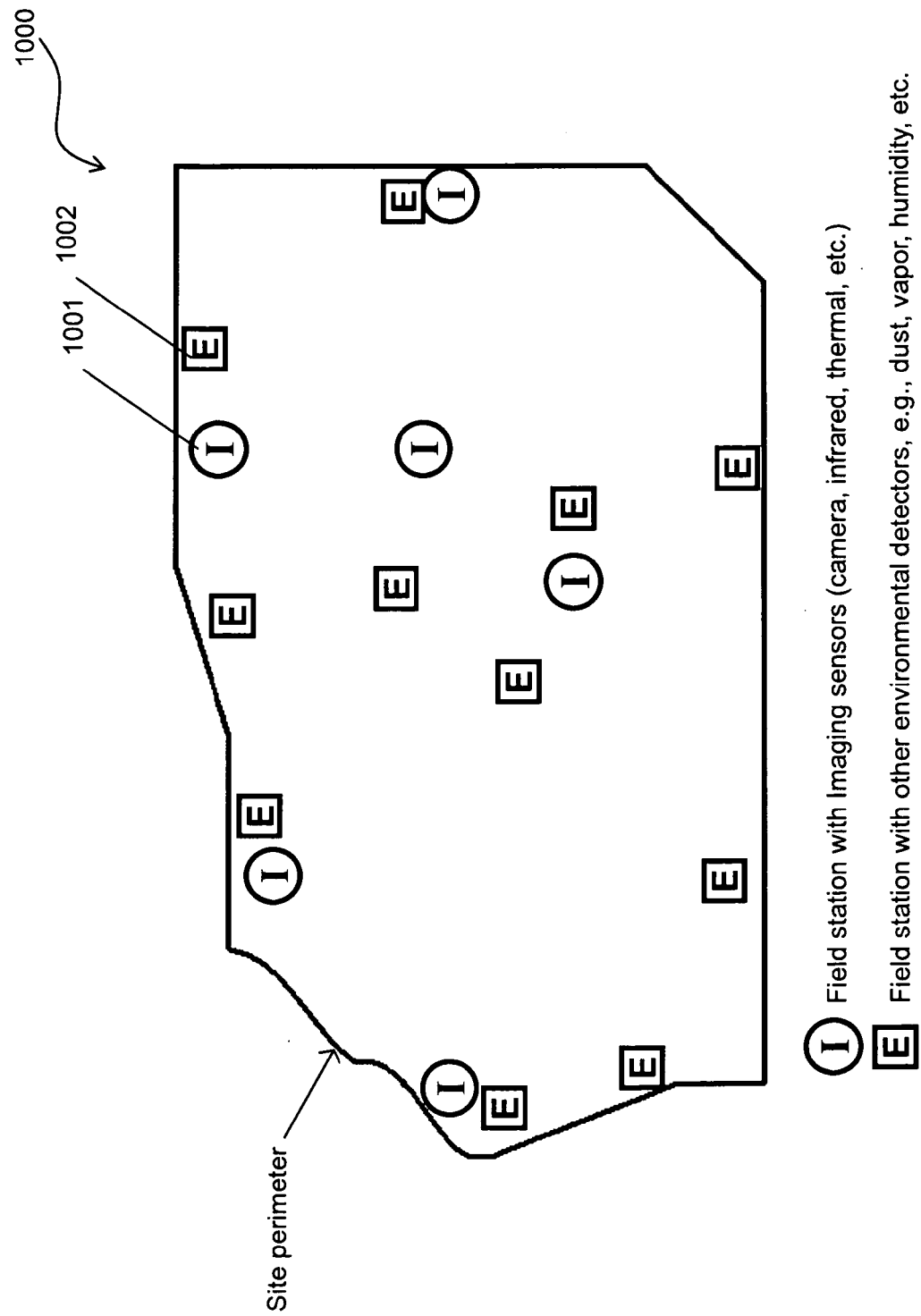
FIG. 10 is a diagram of a map showing a location of instruments related to an environmental monitoring system in accordance with an aspect of the present invention.

The location of imaging devices related to a site being monitored may be displayed on a display under control by the environmental monitoring system. Such displaying may take place in the graphical form of a map 1000 as shown in FIG. 10. Herein the location of imaging devices 1001 may be displayed as an I or as an icon or in any form that is deemed to represent an imaging device or sensor. Other environmental measurement devices 1002 may for instance be identified by an E or by any other symbol, icon or representation that is deemed useful.

Figure 11:
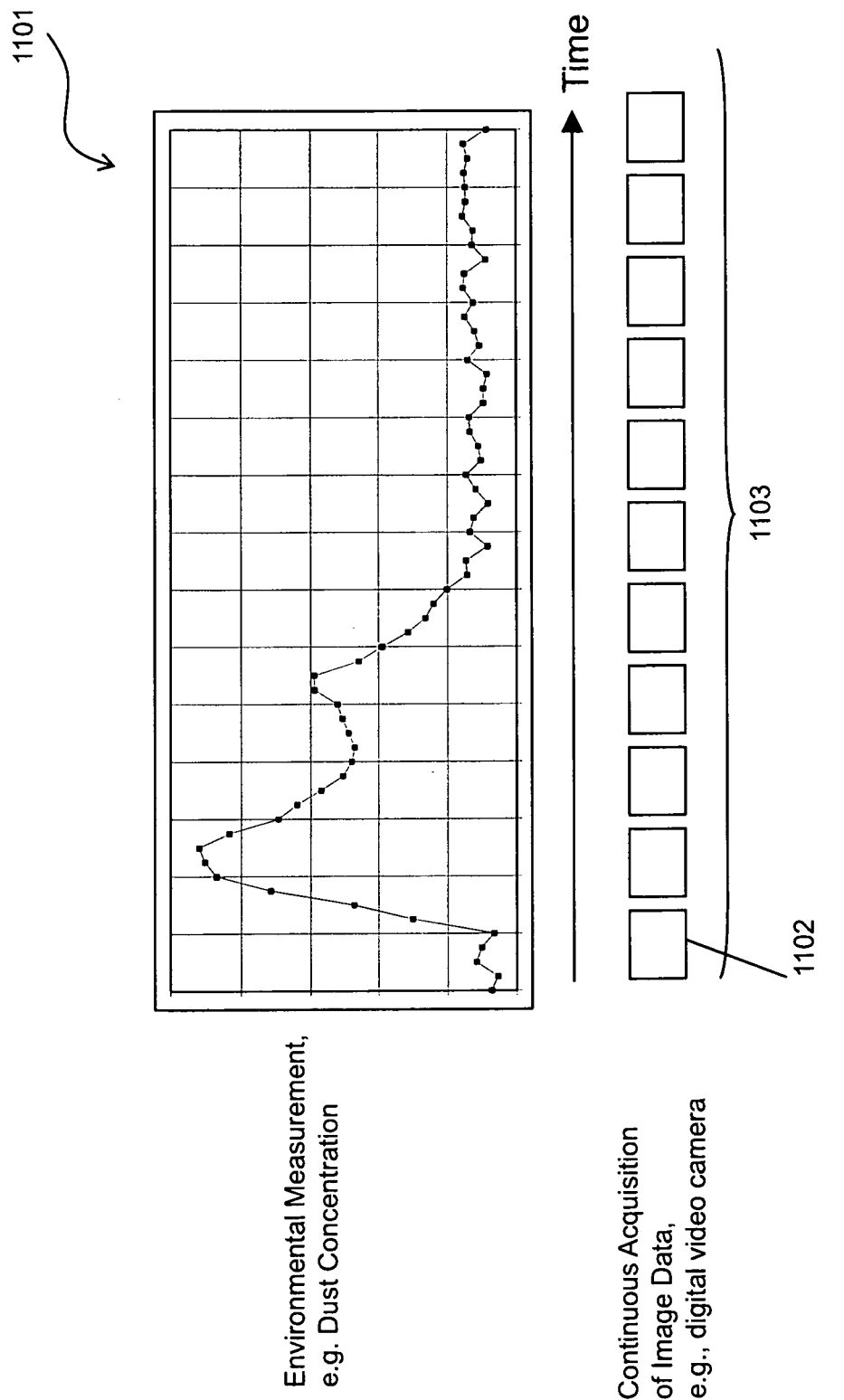
FIG. 11 is a diagram illustrating coordinating an environmental measurement with a plurality of images in accordance with an aspect of the present invention.
Figure 12:
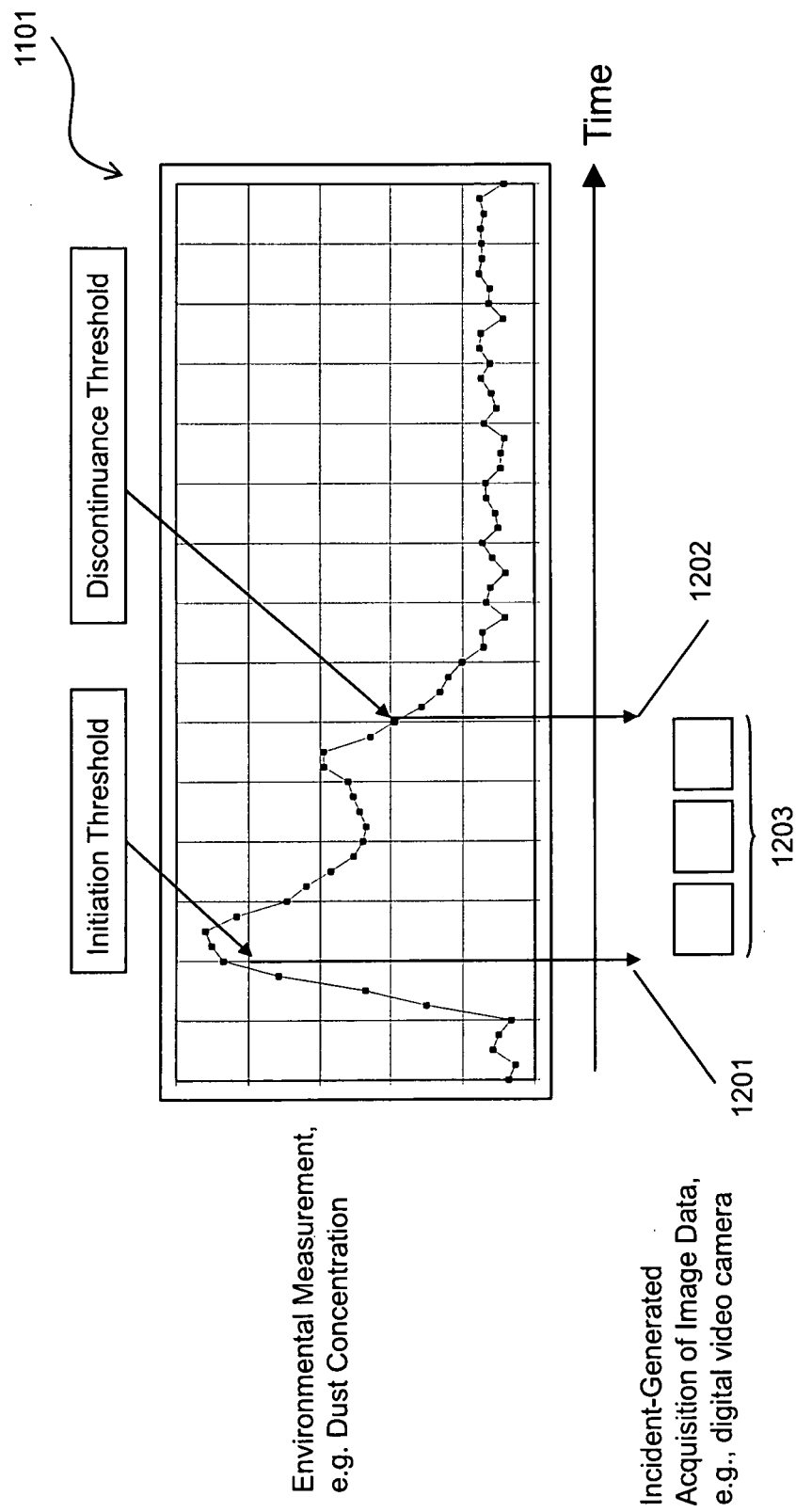
FIG. 12 is another diagram illustrating controlling recording of an image by applying an environmental measurement in accordance with an aspect of the present invention.

Image data can be recorded continuously, with a suitable time-stamp, for either real-time or after-the-fact analysis. Alternatively, acquisition of image data can be started by the environmental monitoring system based for instance on threshold limits established as part of system configuration for the site. This is illustrated in FIGS. 11 and 12. FIG. 11 shows a graph 1101 with a measured concentration of a certain substance at a location of a site. Blocks 1103 represent a series of images over time of a location related to graph 1101. Block 1102 represents a single image or a series of images over a limited time period. In many cases it would not be useful to continually record images of the site. However, it would be useful to start recording images when a certain concentration of material is measured. FIG. 12 illustrates the initiation of recording of images at moment 1201 when a threshold concentration as displayed in graph 1101 is reached. Images remain being recorded as long as the concentration as measured and as displayed in graph 1101 is above level 1202. At or below level 1202 the concentration is assumed to have stopped of being of interest. Between levels 1201 and 1202 a range 1203 of images has been recorded and stored and may be viewed by a user. Images may also be processed by a computer program to detect significant changes. Such computer programs for image analysis are well known and are commercially available.

The measured concentrations 1201 and 1202 are provided with a time stamp. Accordingly, if images are provided with a time stamp one may view those images by searching and correlating time stamps of measured concentrations with recorded and stored images. While as an example a measured concentration of a material is used as a trigger one may use any threshold of a signal provided by a measurement device as a trigger. For instance, one may be concerned at a site with certain wind speeds. Based on a measured wind speed one may start recording and storing images of a site that is being monitored. Any other measured signal provided by the environmental monitoring system that is deemed useful may be applied to initiate recording and storing images of the site and its related areas. Such other measured signals may include, but are not limited to temperature, humidity, concentration of specific materials, measured precipitation over a period of time, radiation, detection of presence of pre-determined concentration levels of a material, detection of the presence of moving objects and/or humans. In addition to reacting to a predetermined threshold of a given measurement, the environmental monitoring system may also react to a rate of change, such as a predetermined amount of change in a particular measured level over a specified interval of time.

An environmental monitoring system may have access to different image recording devices that can record an image of a location related to a site that is being monitored. The recording of an image may start when a certain threshold of data measured by a measurement instrument related to the location. In accordance with an aspect of the present invention only the recording device or recording devices directly observing the location may be started to record images. One may be interested to also see images of locations related to the location of which a measurement threshold was exceeded. For instance, one may want to check if a location upwind has an event that is related to triggering the recording. One may also be interested to see what is happening downwind of the location. One may also be concerned if similar events that triggered the recording may be happening at locations that are deemed to be similar to the location. In accordance with a further aspect of the present invention one may record images at other locations when recording of an image at a location is triggered. One may for instance pre-set criteria that may trigger recording of images at different locations. The system may selectively record images at one or more locations when a recording is triggered.

In accordance with yet another aspect of the present invention, an image may be recorded onto a memory or on a storage medium. The memory may be a mass memory such as a flash memory. The memory may also be any other memory that can store image data. The images may also be stored on mass storage media for digital data such as magnetic media and optical media and other media that can store image data. The images may also be stored on tape such as magnetic tape and tape for optical storage. Information related to recorded images is stored in a database that is part of the system. Images may be searched and if desired displayed based on for instance data related to location, time stamp, duration of recording, related measured data, data that triggered recording of an image, or any other data that is related to the recording of an image by the system.

The system is capable of selectively initiating recording of an image. It is also capable of stopping or suspending recording of an image selectively. The stopping can be based on data provided by a measurement device. Suspending of recording may happen, for instance, when data indicate no or irrelevant change of conditions the system may instruct to only record part of the time. For instance, it may record images for 10 seconds every minute thus reducing the required amount of image data storage space. The period and duration of image recording may be determined by data provided by measurement instruments. For instance, when there is some minimal level of concern indicated by data, the system may record images every 15 minutes for 10 seconds. When there is an increased level of concern the system may record images every 5 minutes for 10 seconds. When there is a significant level of concern the system may record images on a continuous basis.

As a further aspect of the present invention images can be retrieved and displayed by applying search criteria to data associated with recorded images. For instance, one may search and display images from a specific location recorded at a specific day, when certain data such as for example a concentration of a material exceeds a first threshold value. During display of the images one may overlay data from measurement instruments one the image. Such data may be displayed graphically. One may also display a map of the site monitored on the display. On the map at the representation of the location a window may open to display the images of the location. Display windows for showing images from other locations may selectively be opened. Measurement data related to specific locations and/or timestamps may also be displayed.

In a further embodiment one may then display on a display device a map of a site that is being monitored. One may provide a marking on the map of the parts of the site that may be under surveillance of a camera or a recording device. For instance one may provide a color on the map for an area that is associated with a certain recording device. For instance a color may be light blue. The system may change the color to a higher intensity when a recording has been made of an area. A user may click on an area on a map to start the display of a recording. Clicking on an area may also bring up a menu that may provide a user with different options for viewing. In a further embodiment, the system may provide an alert if a recording is available for review. An alert may be a visible alert. It may be an alert provided on a display. It may also be an audible alert.

One may also search for recordings related to a site by providing search criteria. Search criteria may include: if a recording was made during a certain period; recordings lasting more than a certain time; recordings related to certain measurement data such as exceeding a wind speed or exceeding a concentration of particles.

Different systems and methods for detecting and measuring particles as well as recording events and analyzing sources and locations and related methods and events have been provided herein. Different devices and/or systems may be used to generate results as required or desired. In one embodiment of the present invention all devices such as instruments and detectors are part of a network. In a further embodiment, devices are connected to a network via wireless connections. They may also be connected via wired connections or via optical connections. A network in a further embodiment may have a computing device that acts as a controller. One task of a controller may be to manage wireless connections and communication protocols to collect appropriate data from devices in a network and if necessary to instruct devices to perform a task. Network management systems exist to create such networks. Interfaces of devices, wireless and wired, to connect with a network are also known. Instruments and detectors for measuring environmental conditions and for recording events and a computing device for analyzing environmental data and a computing device for generating environmental information and/or alerts may thus be integrated in a network for environmental surveillance and analysis.

In one embodiment one may create such an environmental network in a customized fashion, so that the system and the network which may have wired and/or wireless components is set up for a specific site or a specific purpose or for specific conditions. As a first illustrative example a system may be provided for an outdoors site that is being excavated and that may generate different concentrations of particles. Because of the outdoors situation, instruments such as particle measurement instruments may include a wireless connection to a controller. No biological contaminants may be expected during excavation and so no instruments that can identify such contaminants are included in this network.

In a second illustrative situation, biological contaminants may be expected at the site. In that case the configuration of an existing network may have to be adapted. New instruments may have to be connected to the network. A computer device may have to be reprogrammed or reconfigured to now include processing data provided by a new instrument. Also channels in a network may have to be assigned to include transmitting data generated by a new instrument.

In a further example one may monitor dust particles at different locations inside a building. Perhaps in different rooms or on different floors. One may also want to detect and register the presence of people at a location of a building, for instance when a certain concentration level of dust of a certain particle size is detected.

One may dismantle a facility and one may want to move detection equipment into a certain location at an appropriate time as dismantlement moves on.

It would clearly be an advantage in safety and monitoring of a site and in setting up an environmental network if one can include devices, detectors or instruments at any location, without a need for substantial efforts in a self configuring communication network. In one embodiment of such a network a device, detector or instrument is provided with a standard interface from the device to the network and vice versa. It is assumed, as is often the case, that a device or instrument already has capabilities to exchange data with the outside world. This may be to send data regarding measurement and to receive data for instructions. Such interfaces are well known in the industry for instance as a data acquisition interface. One well known interface for instance is the GPIB interface (IEEE-488.1) standard. Such an interface may be enhanced with a memory device that can store pre-programmed data as well as data received from the outside world or data generated by the instrument that is ready to be transmitted to the outside world.

In a further embodiment of the present invention a device such as a measurement device that is to be connected with an environmental network is provided with means, such as a programmed memory chip, to provide a controller with data. This may be for instance a code that identifies an instrument. Identification may include a functional identification providing information what the device's functional capabilities are. This may further include what function is performed, such as measuring a concentration of particles of a certain size, a chemical substance measuring device, a biological measurement device, a wind speed and direction measurement device, a temperature measurement device, a movement detection device, a camera or any other device which can provide data. The identification may also include range of measurement data, minimum delay time, period of measurement, standard or default alert levels. The device may be able to also provide in a message, operational data next to measurement data which may include time stamp, status of device, maintenance status, location data. Location data may be provided by for instance a GPS device connected with the device. A location may also be derived from a location associated with a port of a network.

In a further embodiment a device may also be enabled to receive instructions, for instance to start measurements or to start transmitting data. It may also receive data that sets internal alert levels and instructs the device to transmit an alert or data whenever a certain measurement level has been surpassed.

In yet a further embodiment a controller of an environmental network may have access to a database which contains data related to possible devices that may be connected to the environmental network. When a device is connected to the network, the controller may receive an identification of the device. The controller can find in the database what the function of the device is, or may receive that data from the device, which can be used to update the database. A location of the device may be provided to update a current location of the device. If the device is for instance a meteorological device, its data may be incorporated by the program that generates for instance a wind map or any other meteorological analysis of the site wherein the environmental network is operational. If the device is a particle or chemical or any other substance measurement device, its output may be incorporated in a relevant analysis and/or display, for instance in a distribution map of particles or substances in a monitored site by for instance time and location.

The function and measurement range of a device is known from its identification. One may call this the operational parameters of a device. This may include standard settings. It may also include a preset alarm level. This is significant because it allows the system or a controller in a system to interpret the data. Without context provided by the identification a device may only provide data of which the meaning is not immediately clear. However, when an instrument is identified it allows for immediate processing of the data. For instance an instrument provides per set period two numbers. Its identification tells the controller that the instrument is a wind measurement instrument that provides new data every 10 seconds as two numbers, of which the first number is a wind direction in a 360 degree polar grid and the second number being an air speed.

A second wind instrument may provide data every 10 minutes, also in two numbers, of which the first number is a speed on a relative scale such as wind force and the second number is a direction in radials. Translation programs allow the translation of units used by instruments into standard units as applied by the system or the controller.

In one embodiment one may provide the instruments with interfaces that translate all data in a standard format. In another embodiment one may provide a controller or the system with the capabilities to translate the units and if needed the dimensions of data.

The identification may also have a default setting for an alert level. When a device is connected it may assume default settings for its operation. In a further embodiment, a controller may require a human operator to set operational parameters, such as alert levels, frequency of reporting, or any other operational parameter before a device in operationally incorporated into an environmental network. A controller may for instance require an authorization to include a device in the network even after the device was identified as being connected to a network.

A device in a network may provide data to which another device may be activated or de-activated. For instance if a wind speed exceeds a certain level, or a particle concentrations exceeds a level, a camera also connected to the network and resident on a location related to the detector, may be activated to provide images that may be recorded. Relationships between activation and deactivation of devices and measurement results of measurement devices may be established in a configurable controller of the network.

The above environmental network allows for quick and simple addition and removal of devices to and from an environmental network. Devices are automatically detected. Any required action to incorporate a device actively into the network can take place automatically by a controller or by a human able to configure the controller, which may take place remotely.

In a further embodiment of the environmental network, the network is the Internet. Its connections may be wired or wireless connections to the Internet. The environmental network may also be comprised of individual networks which are connected to the Internet. Devices may also be connected directly to the Internet. A controller may also be connected directly to the Internet. Devices and devices may communicate via standard Internet compatible message formats such as text messages, XML formatted messages, messages including images, messages including data file attachments, e-mail messages or any other message format that supports exchange of data between a device and a controller and vice versa.

Thus, an easy to configure and to expand environmental network is provided, to which instruments may be added, or from which instruments may be removed without reprogramming controllers of the network. Removal of an instrument or failure of an instrument in a network may be a cause of an alert as to the operational status of the network. In one embodiment one may provide an instrument with a removal status alert. For instance, before removal of an instrument, one may alert the network that the instrument is going off-line. The controller can establish which parts of an analysis will be affected by such a removal and re-set the parts of the system that uses the data from the instruments that is to be removed. In many cases, this will be a reversal to a situation wherein the instrument was not part of the network. In general, this means that the number of data sources for analysis will be reduced. In some cases, the instrument that is to be removed may up to recently have generated data that were critical to an environmental alert. Assuming that an alert situation may still occur, it may not be advisable to remove this particular instrument. The system may generate a signal to the instrument that may trigger a signal like a light or a buzzer or a recorded message, alerting the person not to remove the instrument. In a further embodiment, an operator may instruct the system to disconnect the instrument and reconfigure its analysis routine before the instrument is actually removed.

In a further embodiment, un-authorized removal of an instrument, or failure of an instrument may cause an alert, while it may automatically triggers an adjustment of a system's analysis routine that will no longer be based on data provided by the instrument that was removed or that failed.

In a further embodiment one may generate an analysis of a site based on collected data and provide the analysis on a computer display. One may make such an analysis available to authorized reviewers over the Internet. A reviewer may be authorized to retrieve detailed or specific data provided by the environmental network from a database over the Internet. A reviewer may also be authorized to configure the network from a remote location over the Internet.

In a further embodiment one may operate more than one environmental network over the Internet. Each environmental network may be associated with its own devices, a specific client or project, and if required with its own controller. An operator of environmental networks may operate two or more environmental networks. The two or more environmental network may have a supervisory controller that allows an operator to monitor and maintain the two or more environmental networks, for instance over the Internet.

While there have been shown, described and pointed out fundamental novel features of the invention as applied to preferred embodiments thereof, it will be understood that various omissions and substitutions and changes in the form and details of the methods, devices and systems illustrated and in their operation may be made by those skilled in the art without departing from the spirit of the invention. It is the intention, therefore, to be limited only as indicated by the scope of the claims appended hereto.

The invention claimed is:

1. An environmental monitoring system for a site, comprising:
    a plurality of environmental measuring instruments that collect a plurality of environmental data, including a plurality of measuring instruments being positioned in a location related to the site to be monitored and the plurality of measuring instruments being able to measure a concentration of particles in at least a first range of sizes and in a second range of sizes and provide data related to particles in each of the range of sizes;
    a controller in communication with the plurality of measuring instruments to cause the plurality of data to be transmitted;
    wherein the plurality of environmental data is time stamped and a location of the plurality of environmental measuring instruments is added to the plurality of data; and
    a device located remotely from the plurality of measuring instruments that receives and stores the plurality of environmental data, the time stamp and the location of the plurality of environmental measuring instruments and that displays a map of the site that shows the location of the one or more environmental measuring instruments and the plurality of environmental data generated by each of the one or more environmental measuring instruments including the time stamp on the map, and wherein the device generates a contour indicating an area of a concentration of particles with a size in at least the first range of sizes to determine a location relative to the site of a source that generates the particles from the time stamped and location added data collected by the plurality of environmental measuring instruments.

2. The system as claimed in claim 1, further comprising providing the location with geometric coordinates.

3. The system as claimed in claim 1, wherein the device can display data generated by the plurality of environmental measuring instruments graphically.

4. The system as claimed in claim 1, wherein the device displays a concentration of particles in at least the first range of sizes and in the second range of sizes.

5. The system as claimed in claim 1, wherein the device is enabled to issue an alarm depending on the data generated by the plurality of environmental measuring instrument.

6. The system as claimed in claim 1, further comprising storing in the database an environmental profile of a material including a concentration of at least two ranges of sizes of particles.

7. The system as claimed in claim 6, wherein the alarm is provided when a concentration of at least two ranges of sizes of particles measured by an environmental measurement instrument meets an alarm criterion.

8. The system as claimed in claim 1, wherein the system is enabled to derive from data collected by the plurality of environmental measurement instruments that the location of the source that generates the particles is not within a perimeter of the site.

9. The system as claimed in claim 1, further comprising:
    the system being able to automatically identify operational parameters of at least one of the plurality of environmental measuring instruments when it is connected to the system.

10. The system as claimed in claim 9, further comprising:
    the system being able to process data provided by the at least one of the plurality of environmental measuring instruments based on the operational parameters.

11. A method for monitoring an environment, comprising:
    providing a plurality of environmental measuring instruments that collect a plurality of environmental data, including a plurality of measuring instruments being positioned in a location related to an area to be monitored and the plurality of measuring instruments being able to measure a concentration of particles in at least a first range of sizes and in a second range of sizes and provide data related to particles in each of the range of sizes;

time stamping the plurality of environmental data with a collection time;

adding a location for each of the plurality of environmental measuring instruments that the plurality of data was collected at;

communicating of data between the plurality of environmental measuring instruments and a controller; and determining from data generated simultaneously and in real-time by the plurality of environmental measuring instruments a location relative to the area of a source generating the particles.

12. The method as claimed in claim 11, further comprising determining that the location of the source generating the particles is not within a perimeter of the area.

13. The method as claimed in claim 11, wherein a map of the area displayed on a computer display identifies selectively a location of at least one of the plurality of environmental measurement instruments and displays a concentration of particles in at least the first range of sizes and in the second range of sizes.

14. The method as claimed in claim 11, further comprising: estimating the location of the source of particles.

15. The method as claimed in claim 11, further comprising generating an alarm depending on the data generated by at least one of the plurality of environmental measuring instruments.

16. The method as claimed in claim 11, further comprising:
storing in a database an environmental profile of a material including a concentration of at least two ranges of sizes of particles of the material; and providing an alert based on data collected and the environmental profile.

17. The method as claimed in claim 11, further comprising:
identifying an operational parameter of at least one of the plurality of environmental measuring instruments, when the at least one of the plurality of environmental measuring instruments is connected to a network.

18. The method as claimed in claim 17, further comprising:
processing data provided by the at least one of the plurality of environmental measuring instruments based on the operational parameter.

\* \* \* \* \*